United States Patent
Wang

(10) Patent No.: US 10,071,826 B2
(45) Date of Patent: Sep. 11, 2018

(54) HOT FILL PROCESS WITH CLOSURES MADE FROM HIGH DENSITY POLYETHYLENE COMPOSITIONS

(71) Applicant: NOVA Chemicals (International) S.A., Fribourg (CH)

(72) Inventor: XiaoChuan Wang, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 430 days.

(21) Appl. No.: 15/000,231

(22) Filed: Jan. 19, 2016

(65) Prior Publication Data

US 2017/0166332 A1    Jun. 15, 2017

(30) Foreign Application Priority Data

Dec. 10, 2015 (CA) .................. 2914353

(51) Int. Cl.
| | | |
|---|---|---|
| B67C 3/22 | (2006.01) | |
| B65B 7/28 | (2006.01) | |
| C08L 23/08 | (2006.01) | |
| B65B 3/04 | (2006.01) | |

(52) U.S. Cl.
CPC ............ B65B 7/28 (2013.01); C08L 23/0815 (2013.01); *B65B 3/04* (2013.01); *C08L 2203/10* (2013.01); *C08L 2205/025* (2013.01); *C08L 2205/24* (2013.01); *C08L 2207/06* (2013.01); *C08L 2314/06* (2013.01)

(58) Field of Classification Search
CPC .. B65D 41/00; B65D 41/04; C08J 5/00; C08J 2323/00; C08J 2323/20

USPC ..................................... 53/425, 440
See application file for complete search history.

(56) References Cited

U.S. PATENT DOCUMENTS

| | | | |
|---|---|---|---|
| 3,645,992 A | 2/1972 | Elston | |
| 3,978,063 A * | 8/1976 | Kishimoto | ........... C07D 217/00 514/906 |
| 4,665,682 A * | 5/1987 | Kerins | ............... B29C 49/0005 264/37.31 |
| 4,701,432 A | 10/1987 | Welborn, Jr. | |
| 4,798,081 A | 1/1989 | Hazlitt et al. | |
| 4,808,561 A | 2/1989 | Welborn, Jr. | |
| 4,935,397 A | 6/1990 | Chang | |
| 4,937,301 A | 6/1990 | Chang | |
| 5,055,438 A | 10/1991 | Canich | |
| 5,057,475 A | 10/1991 | Canich et al. | |
| 5,064,802 A | 11/1991 | Stevens et al. | |
| 5,096,867 A | 3/1992 | Canich | |
| 5,132,380 A | 7/1992 | Stevens et al. | |

(Continued)

FOREIGN PATENT DOCUMENTS

| | | |
|---|---|---|
| WO | 93/03093 A1 | 2/1993 |
| WO | 2005/121239 A2 | 12/2005 |

(Continued)

OTHER PUBLICATIONS

Borealis; "Polyolefins Moulding Bottles"; Copyright 2007 by Borealis GmbH pp. 1-16; www.borealisgroup.com.*

(Continued)

*Primary Examiner* — Gloria R Weeks
(74) *Attorney, Agent, or Firm* — Julie L. Heinrich

(57) ABSTRACT

High density (density ≥0.950 g/cm³) polyethylene compositions for use in hot fill closures and processes.

38 Claims, 7 Drawing Sheets

(56) References Cited

U.S. PATENT DOCUMENTS

| | | | |
|---|---|---|---|
| 5,206,075 A | 4/1993 | Hodgson, Jr. | |
| 5,292,845 A | 3/1994 | Kawasaki et al. | |
| 5,324,800 A | 6/1994 | Welborn, Jr. et al. | |
| 5,342,868 A | 8/1994 | Kimura et al. | |
| 5,376,439 A | 12/1994 | Hodgson et al. | |
| 5,633,394 A | 5/1997 | Welborn, Jr. et al. | |
| 5,665,477 A * | 9/1997 | Meathrel | A61B 5/04087 427/2.12 |
| 5,703,187 A | 12/1997 | Timmers | |
| 5,981,636 A | 11/1999 | Amos et al. | |
| 6,002,033 A | 12/1999 | Razavi et al. | |
| 6,034,021 A | 3/2000 | Wilson et al. | |
| 6,063,879 A | 5/2000 | Stephan et al. | |
| 6,114,481 A | 9/2000 | McMeeking et al. | |
| 6,235,672 B1 | 5/2001 | McKay et al. | |
| 6,277,931 B1 | 8/2001 | Jaber et al. | |
| 6,342,463 B1 | 1/2002 | Stephan et al. | |
| 6,372,864 B1 | 4/2002 | Brown | |
| 6,465,551 B1 | 10/2002 | Zhao et al. | |
| 6,489,413 B1 | 12/2002 | Floyd et al. | |
| 6,502,369 B1 * | 1/2003 | Andison | B65B 3/022 53/275 |
| 6,599,971 B2 | 7/2003 | Dotson et al. | |
| 6,689,847 B2 | 2/2004 | Mawson et al. | |
| 6,777,509 B2 | 8/2004 | Brown et al. | |
| 6,984,695 B2 | 1/2006 | Brown et al. | |
| 7,361,275 B2 * | 4/2008 | Wien | C02F 1/004 210/638 |
| 7,622,550 B2 * | 11/2009 | Cha | C07K 14/43504 530/300 |
| 7,854,104 B2 * | 12/2010 | Cronin | B65D 47/243 206/219 |
| 8,022,143 B2 | 9/2011 | Wang | |
| 8,283,384 B2 * | 10/2012 | Stewart | A61L 24/0015 514/772.1 |
| 8,293,867 B2 * | 10/2012 | Messersmith | B05D 7/52 525/328.2 |
| 8,361,356 B2 * | 1/2013 | Zang | C08L 51/006 264/4.1 |
| 8,567,164 B2 * | 10/2013 | Thomasset | B65D 1/0207 426/401 |
| 8,652,565 B2 * | 2/2014 | Komatsu | G02F 1/167 359/296 |
| 8,907,050 B2 * | 12/2014 | Saleh | C04B 24/28 528/287 |
| 9,074,082 B2 | 7/2015 | Wang et al. | |
| 9,505,893 B2 * | 11/2016 | Wang | C08L 23/0815 |
| 2002/0188053 A1 * | 12/2002 | Zang | C09J 153/00 524/474 |
| 2003/0087338 A1 * | 5/2003 | Messersmith | B82Y 5/00 435/68.1 |
| 2005/0288398 A1 * | 12/2005 | Messersmith | A61L 24/046 524/17 |
| 2006/0247373 A1 | 11/2006 | Goyal et al. | |
| 2008/0247984 A1 * | 10/2008 | Messersmith | C08G 65/3317 424/78.02 |
| 2009/0230079 A1 * | 9/2009 | Smolko | B65D 41/0442 215/261 |
| 2010/0137902 A1 * | 6/2010 | Lee | A61L 24/001 606/213 |
| 2011/0062108 A1 * | 3/2011 | Berthold | C08L 23/06 215/329 |
| 2011/0132864 A1 * | 6/2011 | Jamtvedt | C08K 5/0008 215/329 |
| 2014/0311673 A1 * | 10/2014 | Zhao | C09J 11/02 156/325 |
| 2016/0108185 A1 * | 4/2016 | Wang | C08F 2/001 525/240 |

FOREIGN PATENT DOCUMENTS

| | | |
|---|---|---|
| WO | 2011/050042 A1 | 4/2011 |
| WO | 2015/042561 A1 | 3/2015 |
| WO | 2015/042562 A1 | 3/2015 |
| WO | 2015/042563 A1 | 3/2015 |

OTHER PUBLICATIONS

Wild, L.; Ryle, T.R.; Knobeloch, D.C. and Peat, I.R.; Determination of Branching Distributions in Polyethylene and Ethylene Copolymers; Journal of Polymer Science: Polymer Physics Edition, vol. 20, (1982); pp. 441-455.

Randall, James C.; A Review of High Resolution Liquid 13Carbon Nuclear Magnetic Resonance Characterizations of Ethylene-Based Polymers; JMX-Rev. Macromol. Chem. Phys., C29 (2 & 3), (1989), p. 285.

Hamielec, Archie E.; MacGregor, John F. and Penlidis, Alex; 2. Copolymerization; Comprehensive Polymer Science and Supplements, vol. 3, Chapter 2, (1996); pp. 17-31.

Soares, J.B.P. and Hamielec, A.E.; Copolymerization of Olefins in a Series of Continuous Stirred-Tank Slurry-Reactors Using Heterogeneous Ziegler-Natta and Metallocene Catalysts. I. General Dynamic Mathematical Model; Polymer Reaction Engineering, 4 (2 & 3); (1996); pp. 153-191.

Wang, XiaoChuan (Alan); Deformation Measurement, Modeling and Morphology Study for HDPE Caps and Closures; ANTEC publication; Mar. 23-25, 2015; Orlando, FL; pp. 1-5.

ASTM D2990-09; Standard Test Methods for Tensile, Compressive, and Flexural Creep and Creep-Rupture of Plastics; ASTM International; pp. 1-20.

ASTM D6474-99 (Reapproved 2006); Standard Test Method for Determining Molecular Weight Distribution and Molecular Weight Averages of Polyolefins by High Temperature Gel Permeation Chromatography; ASTM International; pp. 1-6.

ASTM D792-13; Standard Test Methods for Density and Specific Gravity (Relative Density) of Plastics by Displacement; ASTM International; pp. 1-6.

ASTM D1238-10; Standard Test Method for Melt Flow Rates of Thermoplastics by Extrusion Plastometer; ASTM International; pp. 1-15.

ASTM D1693-12; Standard Test Method for Environmental Stress-Cracking of Ethylene Plastics; ASTM International; pp. 1-11.

ASTM D256-10; Standard Test Methods for Determining the Izod Pendulum Impact Resistance of Plastics; ASTM International; pp. 1-19.

ASTM D6645-01; Standard Test Method for Methyl (Comonomer) Content in Polyethylene by Infrared Spectrophotometry; ASTM International; pp. 1-4.

ASTM D3124-98; Standard Test Method for Vinylidene Unsaturation in Polyethylene by Infrared Spectrophotometry; ASTM International; pp. 1-4.

ASTM D5227-01 (Reapproved 2008); Standard Test Method for Measurement of Hexane Extractable Content of Polyolefins; ASTM International; pp. 1-4.

ASTM D790-10; Standard Test Methods for Flexural Properties of Unreinforced and Reinforced Plastics and Electrical Insulating Materials; ASTM International; pp. 1-11.

ASTM D638-10; Standard Test Method for Tensile Properties of Plastics; ASTM International; pp. 1-16.

ASTM D648-07; Standard Test Method for Deflection Temperature of Plastics Under Flexural Load in the Edgewise Position; ASTM International; pp. 1-13.

ASTM D1525-09; Standard Test Method for Vicat Softening Temperature of Plastics; ASTM International; pp. 1-10.

* cited by examiner

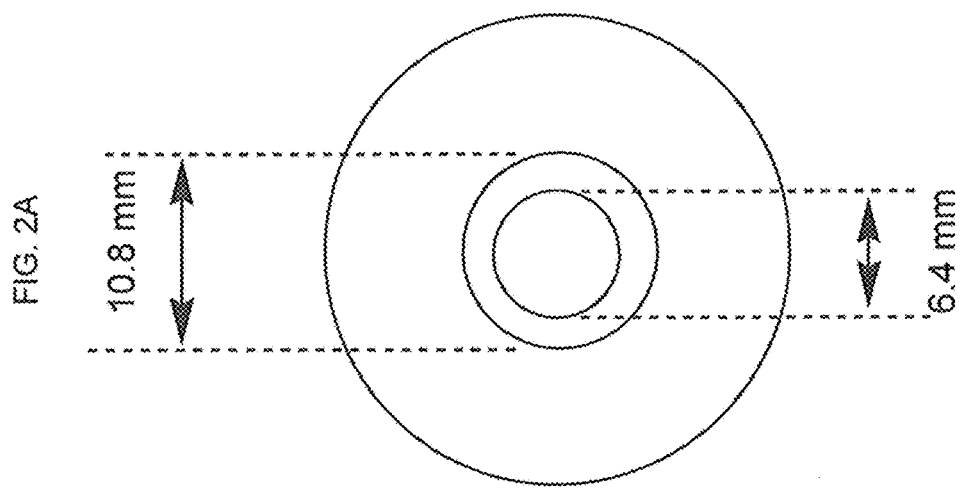

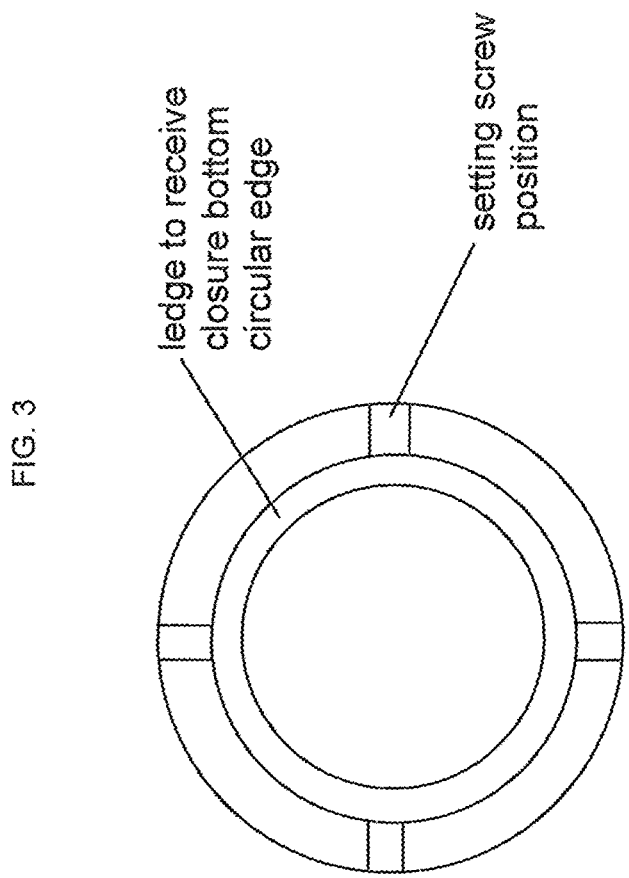

HOT FILL PROCESS WITH CLOSURES MADE FROM HIGH DENSITY POLYETHYLENE COMPOSITIONS

The present disclosure relates to a hot filling process which employs closures made from high density (density ≥0.950 g/cm$^3$) polyethylene compositions.

Hot filling techniques are commonly used in the bottling of beverages such as, for example, drinks, fruit juices, milk, tea, sports drinks and flavored water. Typically, the material employed to package these materials in a hot fill application is polyethylene terephthalate (PET). PET bottles are light weight and tough.

A typical hot fill process involves the following steps. A hot liquid beverage is added to a plastic bottle while at an elevated temperature, typically from about 70 to about 93° C. under a positive pressure and over a 15 to 30 second time interval. The bottle or container is then immediately sealed with a plastic closure and tilted on its side or inverted. Contact of the hot liquid with the closure sterilizes the closure. Inversion may last for example, about 15 seconds, or a time sufficient for sterilization of the closure interior. Following sterilization of the closure interior, the bottle may be cooled to for example about 40° C.

In order to be properly applicable to a hot filling process the closure should be made of a material that imparts heat resistance (e.g. resistance to deformation during hot/cold cycles occurring in a hot filling process), good sealing properties to prevent leaking, and resistance to the development of cracks.

As discussed in a recent ANTEC® publication, "*Deformation Measurement, Modeling and Morphology Study for HDPE Caps and Closures*", by XiaoChuan (Alan) Wang, Mar. 23-25, 2015, Orlando, Fla., USA, it is difficult to directly study the deformation properties of plastic closures due to their complex geometries and relatively small dimensions. Standard tests for creep properties (e.g. tensile creep, flexural creep, and compressive creep) such as those described in ASTM D-2990 employ standard compression molded specimens or plaques, not caps or closures per se. Further, the final polymer morphology, as it exists in a molded closure formed from injection molding or continuous compression molding techniques, may not be represented when using standardized testing which employ standardized plaques. As such, a method which informs about the deformation properties of a finished closure was developed. The method employed a model to evaluate the deformation of an "as is closure" at different instantaneous stresses, times and temperatures. To properly model the closure deformation, any tamper-evident ring attached to the closure was removed.

We have now found that application of the methodology and model to closures comprising high density polyethylene compositions allows one to select for polymer compositions which are particularly suitable for application in hot fill closures and processes.

The present disclosure shows that certain high density polyethylene compositions are suitable for making closures used in hot fill processes.

The preset disclosure also contemplates the use of high density polyethylene compositions for use in aseptic fill processes.

A recently developed model and a series of tests are used to demonstrate those closure characteristics which are suitable for hot fill, or aseptic fill applications.

Provided is a process to fill a container, the process comprising: adding a hot liquid to the container through a container opening, sealing the container opening with a closure comprising a high density polyethylene composition which is bimodal and has a density of at least 0.950 g/cm$^3$, a molecular weight distribution $M_w/M_n$, of from 2.0 to 7.0, and a melt index $I_2$, of from higher than 3.0 g/10 min to less than 20.0 g/10 min; and bringing the hot liquid into contact with an interior surface of the closure.

Provided is a process to fill a container, the process comprising: adding a hot liquid to the container through a container opening, sealing the container opening with a closure comprising a high density polyethylene composition, and bringing the hot liquid into contact with an interior surface of the closure; wherein the high density polyethylene composition comprises:

(1) about 10 to about 70 wt % of a first ethylene copolymer having a melt index $I_2$, of from 0.1 to 10 g/10 min; a molecular weight distribution $M_w/M_n$, of less than 2.7; and a density of from 0.930 to 0.960 g/cm$^3$; and (2) about 90 to about 30 wt % of a second ethylene copolymer having a melt index $I_2$, of from 50 to 10,000 g/10 min; a molecular weight distribution $M_w/M_n$, of less than 2.7; and a density higher than the density of the first ethylene copolymer, but less than 0.966 g/cm$^3$;

wherein the density of the second ethylene copolymer is less than 0.037 g/cm$^3$ higher than the density of the first ethylene copolymer; the ratio (SCB1/SCB2) of the number of short chain branches per thousand carbon atoms in the first ethylene copolymer (SCB1) to the number of short chain branches per thousand carbon atoms in the second ethylene copolymer (SCB2) is greater than 1.0; and wherein the high density polyethylene composition has a molecular weight distribution $M_w/M_n$, of from 2.0 to 7.0; a density of at least 0.950 g/cm$^3$; and a melt index $I_2$, of greater than 3.0 to less than 20.0 g/10 min.

Use of a closure in a hot fill process is provided, wherein the closure comprises a high density polyethylene composition which is bimodal and has a density of at least 0.950 g/cm$^3$, a molecular weight distribution $M_w/M_n$, of from 2.0 to 7.0, and a melt index $I_2$, of from higher than 3.0 g/10 min to less than 20.0 g/10 min.

A use of a closure in a hot fill process is provided, wherein the closure comprises a high density polyethylene composition comprising:

(1) about 10 to about 70 wt % of a first ethylene copolymer having a melt index $I_2$, of from 0.1 to 10 g/10 min; a molecular weight distribution $M_w/M_n$, of less than 2.7; and a density of from 0.930 to 0.960 g/cm$^3$; and (2) about 90 to about 30 wt % of a second ethylene copolymer having a melt index $I_2$, of from 50 to 10,000 g/10 min; a molecular weight distribution $M_w/M_n$, of less than 2.7; and a density higher than the density of the first ethylene copolymer, but less than 0.966 g/cm$^3$;

wherein the density of the second ethylene copolymer is less than 0.037 g/cm$^3$ higher than the density of the first ethylene copolymer; the ratio (SCB1/SCB2) of the number of short chain branches per thousand carbon atoms in the first ethylene copolymer (SCB1) to the number of short chain branches per thousand carbon atoms in the second ethylene copolymer (SCB2) is greater than 1.0; and wherein the high density polyethylene composition has a molecular weight distribution $M_w/M_n$, of from 2.0 to 7.0; a density of at least 0.950 g/cm$^3$; and a melt index $I_2$, of greater than 3.0 to less than 20.0 g/10 min.

Provided is a process to fill a container, the process comprising: adding a hot liquid to the container through a container opening; sealing the container opening with a closure comprising a high density polyethylene composition which is bimodal and has a density of at least 0.950 g/cm$^3$, a molecular weight distribution $M_w/M_n$, of from 2.0 to 7.0, and a melt index $I_2$, of from higher than 3.0 g/10 min to less than 20.0 g/10 min; and bringing the hot liquid into contact with an interior surface of the closure; wherein the closure has a time exponent, m of 0.105 or less where m is determined using a compressive strain model represented by the equation:

$$\varepsilon = A \times \sigma^n \times t^m$$

where $\varepsilon$ is the compressive strain; $\sigma$ is the stress in N/cm$^2$, t is the loading time in seconds, A is the model coefficient, n is the deformation stress exponent and m is the time exponent.

Provided is a process to fill a container, the process comprising: adding a hot liquid to the container through a container opening; sealing the container opening with a closure comprising a high density polyethylene composition; and bringing the hot liquid into contact with an interior surface of the closure; wherein the closure has a time exponent, m of 0.105 or less where m is determined using a compressive strain model represented by the equation:

$$\varepsilon = A \times \sigma^n \times t^m$$

where $\varepsilon$ is the compressive strain; $\sigma$ is the stress in N/cm$^2$, t is the loading time in seconds, A is the model coefficient, n is the deformation stress exponent and m is the time exponent; and wherein the high density polyethylene composition comprises:

(1) about 10 to about 70 wt % of a first ethylene copolymer having a melt index $I_2$, of from 0.1 to 10 g/10 min; a molecular weight distribution $M_w/M_n$, of less than 2.7; and a density of from 0.930 to 0.960 g/cm$^3$; and (2) about 90 to about 30 wt % of a second ethylene copolymer having a melt index $I_2$, Of from 50 to 10,000 g/10 min; a molecular weight distribution $M_w/M_n$, of less than 2.7; and a density higher than the density of the first ethylene copolymer, but less than 0.966 g/cm$^3$;

wherein the density of the second ethylene copolymer is less than 0.037 g/cm$^3$ higher than the density of the first ethylene copolymer; the ratio (SCB1/SCB2) of the number of short chain branches per thousand carbon atoms in the first ethylene copolymer (SCB1) to the number of short chain branches per thousand carbon atoms in the second ethylene copolymer (SCB2) is greater than 1.0; and wherein the high density polyethylene composition has a molecular weight distribution $M_w/M_n$, of from 2.0 to 7.0; a density of at least 0.950 g/cm$^3$; and a melt index $I_2$, of greater than 3.0 to less than 20.0 g/10 min.

Use of a closure in a hot fill process is provided, wherein the closure comprises a high density polyethylene composition which is bimodal and has a density of at least 0.950 g/cm$^3$, a molecular weight distribution $M_w/M_n$, of from 2.0 to 7.0, and a melt index $I_2$, of from higher than 3.0 g/10 min to less than 20.0 g/10 min; wherein the closure has a time exponent, m of 0.105 or less, where m is determined using a compressive strain model represented by the equation:

$$\varepsilon = A \times \sigma^n \times t^m$$

where $\varepsilon$ is the compressive strain; $\sigma$ is the stress in N/cm$^2$, t is the loading time in seconds, A is the model coefficient, n is the deformation stress exponent and m is the time exponent.

Use of a closure in a hot fill process is provided, wherein the closure comprises a high density polyethylene composition; wherein the closure has a time exponent, m of 0.105 or less, where m is determined using a compressive strain model represented by the equation:

$$\varepsilon = A \times \sigma^n \times t^m$$

where $\varepsilon$ is the compressive strain; $\sigma$ is the stress in N/cm$^2$, t is the loading time in seconds, A is the model coefficient, n is the deformation stress exponent and m is the time exponent; and wherein the high density polyethylene composition comprises:

(1) about 10 to about 70 wt % of a first ethylene copolymer having a melt index $I_2$, of from 0.1 to 10 g/10 min; a molecular weight distribution $M_w/M_n$, of less than 2.7; and a density of from 0.930 to 0.960 g/cm$^3$; and (2) about 90 to about 30 wt % of a second ethylene copolymer having a melt index $I_2$, of from 50 to 10,000 g/10 min; a molecular weight distribution $M_w/M_n$, of less than 2.7; and a density higher than the density of the first ethylene copolymer, but less than 0.966 g/cm$^3$;

wherein the density of the second ethylene copolymer is less than 0.037 g/cm$^3$ higher than the density of the first ethylene copolymer; the ratio (SCB1/SCB2) of the number of short chain branches per thousand carbon atoms in the first ethylene copolymer (SCB1) to the number of short chain branches per thousand carbon atoms in the second ethylene copolymer (SCB2) is greater than 1.0; and wherein the high density polyethylene composition has a molecular weight distribution $M_w/M_n$, of from 2.0 to 7.0; a density of at least 0.950 g/cm$^3$; and a melt index $I_2$, of greater than 3.0 to less than 20.0 g/10 min.

BRIEF DESCRIPTION OF THE DRAWINGS

FIGS. 1A and 1B show gel permeation chromatographs for the unimodal polyethylene compositions used in Examples 1 and 2 respectively.

FIG. 1C shows a gel permeation chromatograph for the bimodal polyethylene composition used in Example 3.

FIG. 2A. FIG. 2A shows a plan view of the probe used in the closure deformation testing. The view shows the bottom side of the probe which contacts the upper surface of the closure FIG. 2B.

FIG. 3. FIG. 3 shows a plan view (with screw locations indicated) of the closure holder used in deformation stress testing. The view shows the upper surface of the holder which receives the lower annular edge of the closure.

FIG. 4 shows actual and fitted compressive deformation data for the closures of Example 1 and Example 3.

Filling Process

Figure 1A:
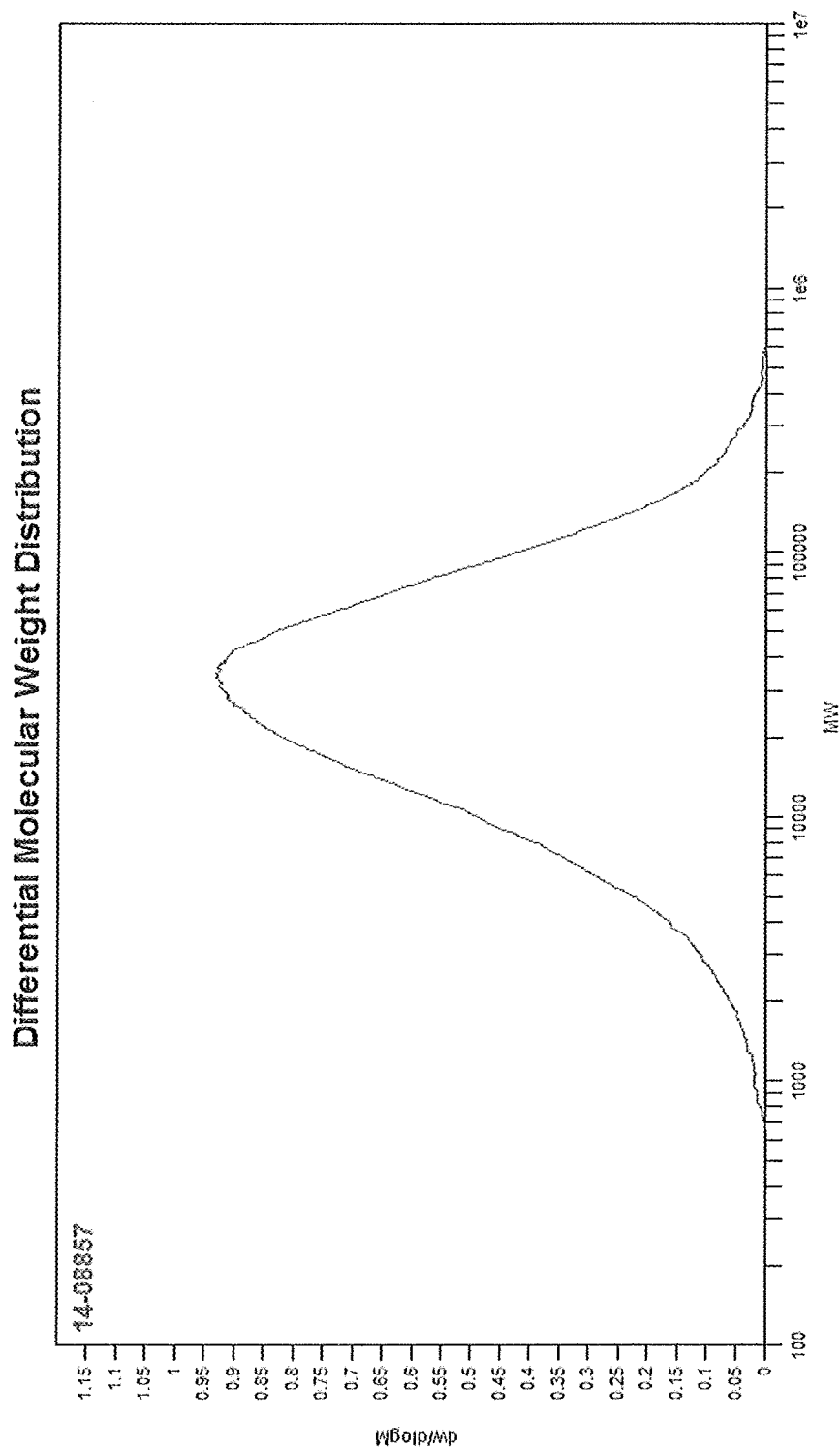
FIGS. 1A and 1B.
Figure 1B:
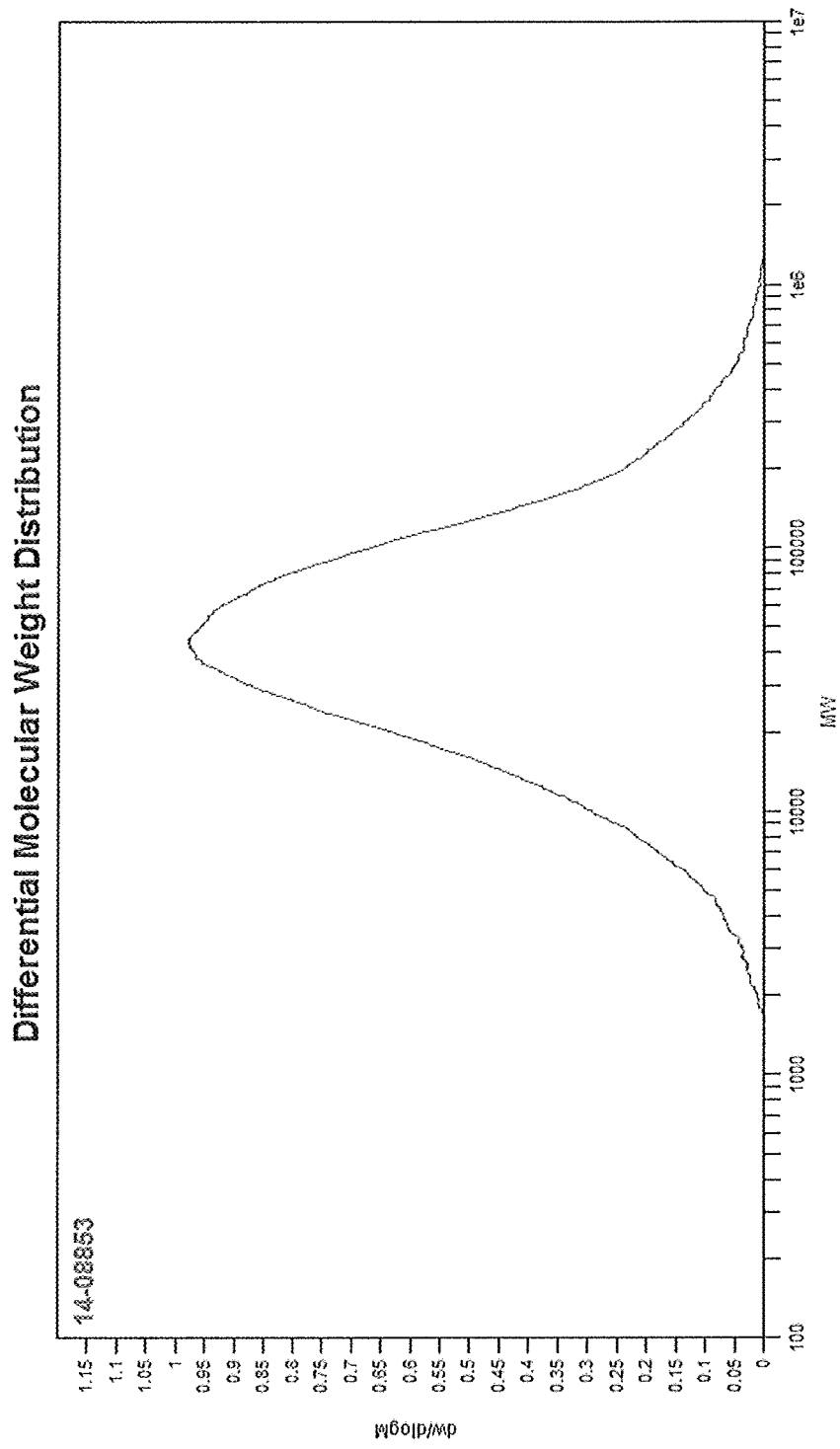
Figure 1C:
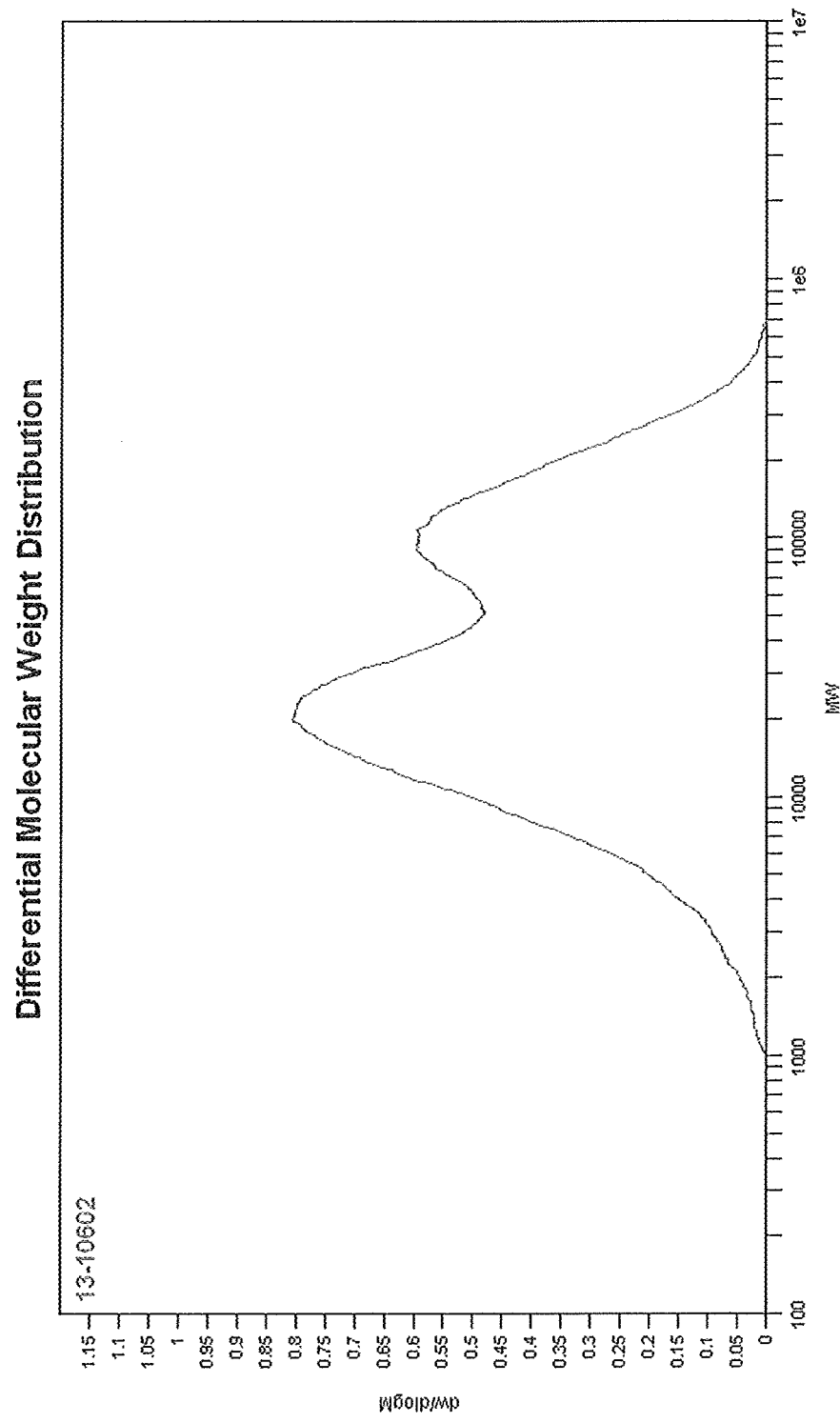
FIG. 1C.
Figure 2B:
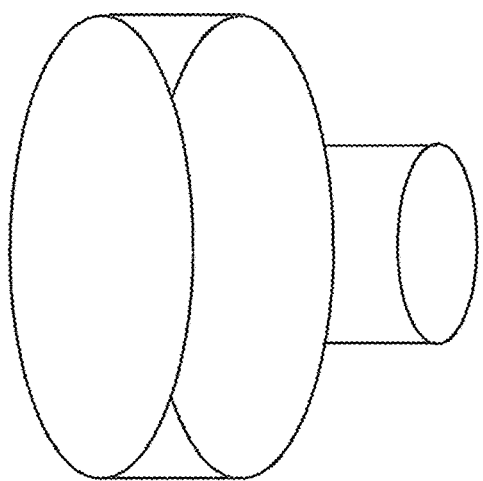
FIG. 2B shows a partially transparent perspective view of the probe used in the closure deformation testing.

The present disclosure is concerned with the use of closures in filling/sealing processes which have at least one step in which the closure interior (and optionally the container, bottle and the like) is (are) contacted with a liquid at elevated temperatures, or temperatures above ambient, or above room temperature or above about 20° C., or any temperature high enough to destroy microorganisms which may lead to illness when consumed (e.g. temperatures high enough to sterilize the closure and/or pasteurize the liquid). Processes which involve steps in which a closure is used to seal a container, bottle and the like containing a liquid at an elevated temperature include for example hot fill processes and in some cases aseptic fill processes. The disclosure is not limited to any particular end use or process so long as a closure is contacted with a liquid at elevated temperatures for the end use or during the process and is used to seal a container, bottle and the like.

In the present disclosure the terms "hot liquid" and "hot beverage" are used interchangeably, and connote that a liquid that has been heated to above ambient temperature or room temperature or above about 20° C., or any temperature high enough to destroy microorganisms which may lead to illness when consumed (e.g. temperatures high enough to pasteurize the liquid or beverage).

In embodiments of the disclosure, a hot liquid is a liquid that has been heated to from about 21° C. to about 150° C., and further including all numbers and narrower ranges within this range such as for example from about 70° C. to about 150° C., or from about 70° C. to about 145° C., or from about 80° C. to about 150° C., or from about 80° C. to about 145° C., or from about 21° C. to about 100° C., or from about 30° C. to about 100° C., or from about 30° C. to about 98° C., or from about 30° C. to about 95° C., or from about 30° C. to about 93° C., or from about 50° C. to about 100° C., or from about 50° C. to about 98° C., or from about 50° C. to about 95° C., or from about 50° C. to about 93° C., or from about 60° C. to about 100° C., or from about 60° C. to about 98° C., or from about 60° C. to about 95° C., or from about 60° C. to about 93° C., or from about 70° C. to about 100° C., or from about 70° C. to about 98° C., or from about 70° C. to about 95° C., or from about 70° C. to about 93° C.

The term "interior surface" as it is applied to a cap or closure is any part of the closure interior that may come into contact with a hot liquid during a filling process.

An embodiment of the disclosure is a process to fill a container, the process comprising: adding a hot liquid to the container through a container opening, sealing the container opening with a closure comprising a high density polyethylene composition, and bringing the hot liquid into contact with an interior surface of the closure.

An embodiment of the present disclosure is a process to fill a container, the process comprising: adding a hot liquid to the container through a container opening, sealing the container opening with a closure comprising a high density polyethylene composition which is bimodal and has a density of at least 0.950 g/cm$^3$, a molecular weight distribution $M_w/M_n$, of from 2.0 to 7.0, and a melt index $I_2$, of from higher than 3.0 g/10 min to less than 20.0 g/10 min; and bringing the hot liquid into contact with an interior surface of the closure.

Hot Fill Process

A hot fill process is often used in an automated container filling line. Use of the hot fill process is often the process of choice for juices, beverages and the like since it eliminates the need for the addition of chemicals and preservatives while maintaining the same shelf life and nutritional properties of the beverage. Consumers are often wary of the presence of preservatives and chemicals, and so hot filling processes provide a useful alternative.

The hot filling process can be used in combination with any suitable beverages, including vegetable and fruit juice, dairy products such as milk, flavored waters, sports drinks and the like.

A hot fill process comprises a series of steps. Ideally the steps are optimized to provide shorter container fill times while still providing acceptable beverage shelf life in the absence of added chemicals or preservatives. The steps are generally incorporated into a container or bottle fill line and generally comprise:

Step 1) A beverage is heated to the desired hot filling temperature. The temperatures employed are not specifically defined herein, but by way of non-limiting example only, can be from about 70° C. to about 95° C. Suitable temperatures include those which are known to kill microorganisms which may cause illness (e.g., temperatures at which the beverage or liquid is pasteurized). The beverage may be heated using any known device, such as but not limited to a heat exchanger, and may be heated in a continuous or batch manner. The beverage may be heated for any suitable time which is known to kill the microorganisms which may be present in the liquid. By way of a non-limiting examples, the beverage may be heated by passage through a heat exchanger for at least 10, or at least 15, or at least 20 seconds.

Step 2) A container is filled with the hot beverage using a suitable filling apparatus, followed by the addition of a closure. By hot filling the container, the container interior is sterilized by the hot beverage. Although the closure should be added immediately once the container is hot filled, nitrogen may be introduced into the head space to displace unwanted oxygen prior to the addition of the closure. Optionally, and before the container is filled with the hot beverage, the temperature of the liquid may be reduced slightly. By way of providing a non-limiting example only, the temperature of the beverage may be reduced to from about 80° C. to about less than 90° C.

Step 3) The container is tilted or inverted, or the bottle/closure system moved somehow, so as to bring the hot beverage into contact with the interior surface of the closure. Bringing the hot beverage into contact with the closure interior sterilizes the container interior surfaces.

Step 4) The sealed beverage container and closure may be cooled using a suitable cooling station or apparatus, such as but limited to a shower station or a cooling bath. In embodiments of the disclosure, the container-closure-beverage system is cooled to ambient temperatures or below. In order to preserve the beverage freshness and/or taste, it may be preferable to rapidly cool the container-closure-beverage system. When cooling the sealed container, a vacuum may be created inside the container, further minimizing bacterial growth. Step 4 may also be considered as optional.

Other container fill line process steps known in the art may be used in combination with the above hot fill process steps. For example, the above hot fill process steps may be followed by further cooling, drying and labeling steps.

In an embodiment of the disclosure, the polymer compositions described below are used in the formation of molded articles. For example, articles formed by continuous compression molding and injection molding are contemplated. Such articles include, for example, caps, screw caps, and closures for bottles.

In an embodiment of the disclosure a closure is used in a hot fill process, wherein the closure comprises a high density polyethylene composition which is bimodal and has a density of at least 0.950 g/cm$^3$, a molecular weight distribution $M_w/M_n$, of from 2.0 to 7.0, and a melt index $I_2$, of from higher than 3.0 g/10 min to less than 20.0 g/10 min.

Container (e.g., Bottle)

The material used for the container (or bottle and the like) is not specifically defined, but by way of providing a non-limiting example only, the material may be polyethylene terephthalate (PET). In another embodiment the container (e.g. bottle) may be made of glass. It should be understood that by use of the word "container" that any suitably shaped vessel, bottle, pouch and the like, may be used in the present invention, so long as they can store a liquid, and have a suitable aperture or structure which allows escape of the liquid and which can be sealed with a closure, cap or the like.

Closures

A closure as described in the present disclosure is a closure suitable for use in a container sealing process comprising one or more steps in which the closure comes into contact with a liquid at elevated temperatures, such as a hot fill processes, and in some cases aseptic fill processes.

The terms "cap" and "closure" are used interchangeably in the current disclosure, and both connote any suitably shaped molded article for enclosing, sealing, closing or covering, etc., a suitably shaped opening, a suitably molded aperture, an open necked structure or the like used in combination with a container, a bottle, a jar, a pouch and the like.

In an embodiment of the disclosure a closure is used in a hot fill process, wherein the closure comprises a high density polyethylene composition which is bimodal and has a density of from 0.950 g/cm$^3$ to 0.960 g/cm$^3$, a molecular weight distribution $M_w/M_n$, of from 2.0 to 7.0, and a melt index $I_2$, of from greater than 3.0 g/10 min to less than 20.0 g/10 min.

Without wishing to be bound by theory, the instantaneous compressive deformation of an "as-is" closure is a function of both instantaneous force (e.g., stress) and time in a non-linear relationship at a given temperature and modeling is required to elucidate the underlying structure-property relationships. The instantaneous compressive deformation model employed in the current disclosure is a compressive strain model represented by the following equation:

$$\varepsilon = A \times \sigma^n \times t^m$$

where $\varepsilon$ is the compressive strain; $\sigma$ is the stress in N/cm$^2$ and t is the loading time in seconds. A is the model coefficient; parameter n is termed the "deformation stress exponent" and m is termed the "time exponent". Any software capable of performing non-linear regressions can be used to estimate the model parameters. Such a compressive deformation model was recently disclosed at an ANTEC meeting as "*Deformation Measurement, Modeling and Morphology Study for HDPE Caps and Closures*", XiaoChuan (Alan) Wang, Mar. 23-25, 2015, Orlando, Fla., USA.

In an embodiment of the present disclosure, a closure has a time exponent, m of 0.105 or less where m is determined using a compressive strain model represented by the equation:

$$\varepsilon = A \times \sigma^n \times t^m$$

where $\varepsilon$ is the compressive strain; $\sigma$ is the stress in N/cm$^2$, t is the loading time in seconds, A is the model coefficient, n is the deformation stress exponent and m is the time exponent.

In further embodiments of the present disclosure, a closure has a time exponent, m of 0.105 or less, or ≤0.0955, or ≤0.0910, or ≤0.0875, or ≤0.0850, or ≤0.0825, or ≤0.0800, or ≤0.0775, where m is determined using a compressive strain model represented by the equation:

$$\varepsilon = A \times \sigma^n \times t^m$$

where $\varepsilon$ is the compressive strain; $\sigma$ is the stress in N/cm$^2$, t is the loading time in seconds, A is the model coefficient, n is the deformation stress exponent and m is the time exponent.

In an embodiment of the present disclosure, the closure comprises a high density polyethylene composition which is bimodal and has a density of from 0.950 g/cm$^3$ to 0.960 g/cm$^3$, a molecular weight distribution $M_w/M_n$, of from 2.0 to 7.0, and a melt index $I_2$, of from greater than 3.0 g/10 min to less than 20.0 g/10 min.

In an embodiment of the disclosure, a high density polymer composition is used in the formation of any closure, of any suitable design and dimensions for use in any hot filling process for filling any suitable bottle, container or the like.

In an embodiment of the disclosure, the high density polyethylene compositions described below are used in the formation of a closure for bottles, containers, pouches and the like. For example, closures for bottles formed by continuous compression molding, or injection molding are contemplated. Such closures include, for example, hinged caps, hinged screw caps, hinged snap-top caps, and hinged closures for bottles, containers, pouches, stand-up pouches and the like.

In an embodiment of the disclosure, a closure (or cap) is a screw cap for a bottle, container, pouches and the like.

In an embodiment of the disclosure, a closure (or cap) is a snap closure for a bottle, container, pouches and the like.

In an embodiment of the disclosure, a closure (or cap) comprises a hinge made of the same material as the rest of the closure (or cap).

In an embodiment of the disclosure, a closure (or cap) is hinged closure.

In an embodiment of the disclosure, a closure (or cap) is a hinged closure for bottles, containers, pouches and the like.

In an embodiment of the disclosure, a closure (or cap) is a flip-top hinge closure, such as a flip-top hinge closure for use on a plastic ketchup bottle or similar containers containing foodstuffs.

When a closure is a hinged closure, it comprises a hinged component and generally consists of at least two bodies which are connected by a thinner section that acts as a hinge allowing the at least two bodies to bend from an initially molded position. The thinner section may be continuous or web-like, wide or narrow.

A useful closure (for bottles, containers and the like) is a hinged closure and may consist of two bodies joined to each other by at least one thinner bendable portion (e.g., the two bodies can be joined by a single bridging portion, or more than one bridging portion, or by a webbed portion, etc.). A first body may contain a dispensing hole and which may snap onto or screw onto a container to cover a container opening (e.g., a bottle opening) while a second body may serve as a snap on lid which may mate with the first body.

The caps and closures, of which hinged caps and closures and screw caps are a subset, can be made according to any known method, including for example injection molding and continuous compression molding techniques that are well known to persons skilled in the art. Hence, in an embodiment of the disclosure a closure (or cap) comprising the high density polyethylene composition (defined below) is prepared with a process comprising at least one compression molding step and/or at least one injection molding step.

In one embodiment, the closures (including single piece or multi-piece variants and hinged variants) are well suited for sealing bottles, containers and the like, for example, bottles that may contain drinkable water, and other foodstuffs, including but not limited to liquids that are under an appropriate pressure (i.e., carbonated beverages or appropriately pressurized drinkable liquids).

The closures and caps may also be used for sealing bottles containing drinkable water or non-carbonated beverages (e.g., juice). Other applications, include caps and closures for bottles, containers and pouches containing foodstuffs, such as for example ketchup bottles and the like.

The closures and caps may be one-piece closures or two piece closures comprising a closure and a liner.

The closures and caps may also be of multilayer design, wherein the closure or cap comprises at least two layers at least one of which is made of the high density polyethylene compositions described herein.

In an embodiment of the disclosure the closure is made by continuous compression molding.

In an embodiment of the disclosure the closure is made by injection molding.

High Density Polyethylene Compositions

In the present disclosure, the polyethylene compositions suitable for use in closures for filling processes such as a hot fill process (or any other filling process which comprises at least one step carried out at elevated temperature, such as is the case in some aseptic fill processes) may be chosen based on their tendency to give closures having a combination of good resistance to cracking, sealability and good compressive deformation properties. Direct methods which measure the properties of the closure itself may provide a more accurate representation of the real word performance of a given polyethylene composition for various end use applications.

The term "unimodal" is herein defined to mean there will be only one significant peak or maximum evident in a GPC-curve. A unimodal profile includes a broad unimodal profile. Alternatively, the term "unimodal" connotes the presence of a single maxima in a molecular weight distribution curve generated according to the method of ASTM D6474-99. In contrast, by the term "bimodal" it is meant that there will be a secondary peak or shoulder evident in a GPC-curve which represents a higher or lower molecular weight component (i.e., the molecular weight distribution, can be said to have two maxima in a molecular weight distribution curve). Alternatively, the term "bimodal" connotes the presence of two maxima in a molecular weight distribution curve generated according to the method of ASTM D6474-99. The term "multi-modal" denotes the presence of two or more maxima in a molecular weight distribution curve generated according to the method of ASTM D6474-99.

In an embodiment of the present disclosure, the high density polyethylene compositions are composed of at least two ethylene copolymer components: a first ethylene copolymer and a second ethylene copolymer.

Examples of high density polyethylene compositions which are useful in the present disclosure are disclosed in for example U.S. Pat. No. 9,074,082, which is incorporated herein by reference in its entirety.

It is well known that metallocene catalysts and other so called "single site catalysts" generally incorporate comonomer more evenly than traditional Ziegler-Natta catalysts when used for catalytic ethylene copolymerization with alpha olefins. This fact is often demonstrated by measuring the composition distribution breadth index (CDBI) for corresponding ethylene copolymers. The composition distribution of a polymer can be characterized by the short chain distribution index (SCDI) or composition distribution breadth index (CDBI). The definition of composition distribution breadth index (CDBI(50)) can be found in PCT publication WO 93/03093 and U.S. Pat. No. 5,206,075. The CDBI(50) is conveniently determined using techniques which isolate polymer fractions based on their solubility (and hence their comonomer content). For example, temperature rising elution fractionation (TREF) as described by Wild et al. J. Poly. Sci., Poly. Phys. Ed. Vol. 20, p 441, 1982 or in U.S. Pat. No. 4,798,081 can be employed. From the weight fraction versus composition distribution curve, the CDBI(50) is determined by establishing the weight percentage of a copolymer sample that has a comonomer content within 50% of the median comonomer content on each side of the median. Alternatively, the CDBI(25), which is sometimes used in the art, is determined by establishing the weight percentage of a copolymer sample that has a comonomer content within 25% of the median comonomer content on each side of the median.

The First Ethylene Copolymer

In an embodiment of the disclosure, the first ethylene copolymer of the high density polyethylene composition has a density of from about 0.930 g/cm$^3$ to about 0.960 g/cm$^3$; a melt index, $I_2$, of more than 0.1 g/10 min; a molecular weight distribution, $M_w/M_n$, of below about 3.0 and a weight average molecular weight $M_w$, that is greater than the $M_w$ of the second ethylene copolymer. In one embodiment, the weight average molecular weight $M_w$, of the first ethylene copolymer is at least 50,000 g/mol.

By the term "ethylene copolymer" it is meant that the copolymer comprises both polymerized ethylene and at least one polymerized alpha-olefin comonomer, with polymerized ethylene being the majority species.

In an embodiment of the disclosure, the first ethylene copolymer is made with a single site catalyst, such as, for example, a phosphinimine catalyst.

The comonomer (i.e., alpha-olefin) content in the first ethylene copolymer can be from about 0.05 to about 3.0 mol % as measured by $^{13}$C NMR, or FTIR or GPC-FTIR methods, or as calculated from a reactor model (see the Examples section). The comonomer is one or more suitable alpha olefin, which include, but are not limited to 1-butene, 1-hexene, 1-octene and the like. In one embodiment the alpha olefin is 1-octene.

The short chain branching in the first ethylene copolymer can be from about 0.25 to about 15 short chain branches per thousand carbon atoms (SCB1/1000Cs). In further embodiments of the disclosure, the short chain branching in the first ethylene copolymer can be from 0.25 to 10, or from 0.25 to 7.5, or from 0.25 to 5, or from 0.25 to 3 branches per thousand carbon atoms (SCB1/1000Cs). The short chain branching is the branching due to the presence of alpha-olefin comonomer in the ethylene copolymer and will for example have two carbon atoms for a 1-butene comonomer, or four carbon atoms for a 1-hexene comonomer, or six carbon atoms for a 1-octene comonomer, etc. The comonomer is one or more suitable alpha-olefin, which include, but are not limited to, 1-butene, 1-hexene, 1-octene and the like. In one embodiment the alpha olefin is 1-octene.

In an embodiment of the disclosure, the comonomer content in the first ethylene copolymer is greater than comonomer content of the second ethylene copolymer (as reported, for example, in mol %).

In an embodiment of the disclosure, the amount of short chain branching in the first ethylene copolymer is greater than the amount of short chain branching in the second ethylene copolymer (as reported in short chain branches, SCB per thousand carbons in the polymer backbone, 1000 Cs).

In some embodiments of the disclosure the melt index, $I_2$, of the first ethylene copolymer can be from 0.1 to 10 g/10 min and including narrower ranges within this range and any numbers encompassed by these ranges. For example, the melt index $I_2$ of the first ethylene composition can be from above 0.1 to below 10 g/10 min, or can be from 0.1 to 7.5 g/10 min, or from 0.1 to 5.0 g/10 min, or from 0.1 to 3.0 g/10 min, or from 0.1 to 2.5 g/10 min, or from 0.1 to 1.0 g/10 min.

In an embodiment of the disclosure, the first ethylene copolymer has a weight average molecular weight $M_w$ of from about 50,000 to about 225,000 g/mol including narrower ranges and any numbers encompassed by these ranges. For example, in another embodiment of the disclosure, the first ethylene copolymer has a weight average molecular weight $M_w$ of from about 75,000 to about 200,000. In further embodiments of the disclosure, the first ethylene copolymer has a weight average molecular weight $M_w$ of from about 75,000 to about 175,000, or from about 85,000 to about 150,000, or from about 100,000 to about 150,000.

The density of the first ethylene copolymer is in the present disclosure from 0.930 to 0.960 g/cm$^3$ or can be a narrower range within this range and any numbers encompassed by these ranges. For example, in further embodiments of the disclosure, the density of the first ethylene copolymer can be from 0.936 to 0.960 g/cm$^3$, or can be from 0.938 to 0.960 g/cm$^3$, or from 0.936 to 0.952 g/cm$^3$, or from 0.938 to 0.952 g/cm$^3$, or from 0.936 to 0.950 g/cm$^3$, or from 0.938 to 0.950 g/cm$^3$, or from 0.936 to 0.947 g/cm$^3$, or from 0.938 to 0.947 g/cm$^3$, or from 0.936 to 0.945 g/cm$^3$, or from 0.938 to 0.945 g/cm$^3$.

In embodiments of the disclosure, the first ethylene copolymer has a molecular weight distribution $M_w/M_n$ of <3.0, or ≤2.7, or <2.7, or ≤2.5, or <2.5, or ≤2.3, or from 1.8 to 2.3.

The $M_w/M_n$ value of the first ethylene copolymer can in an embodiment of the disclosure be estimated by a deconvolution of a GPC profile obtained for a bimodal polyethylene composition of which the first ethylene copolymer is a component.

In an embodiment of the disclosure, the first ethylene copolymer of the high density polyethylene composition is produced with a single site catalyst and has a weight average molecular weight $M_w$, of at least 50,000 g/mol; a molecular weight distribution, $M_w/M_n$, of less than 3.0 and a density of from 0.936 to 0.950 g/cm$^3$.

In an embodiment of the disclosure, a single site catalyst which gives an ethylene copolymer having a CDBI(50) of at least about 65% by weight, or at least about 70%, or at least about 75%, or at least about 80%, or at least about 85%, during solution phase polymerization in a single reactor, is used in the preparation of the first ethylene copolymer.

In an embodiment of the present disclosure, the first ethylene copolymer is ethylene copolymer which has a CDBI(50) of greater than about 60% by weight, or greater than about 65%, or greater than about 70%, or greater than about 75%, or greater than about 80%, or greater than about 85%.

The first ethylene copolymer can comprise from about 10 to about 70 weight percent (wt %) of the total weight of the first and second ethylene copolymers. In an embodiment of the disclosure, the first ethylene copolymer comprises from 20 to about 60 weight percent (wt %) of the total weight of the first and second ethylene copolymers. In an embodiment of the disclosure, the first ethylene copolymer comprises from about 25 to about 60 weight percent (wt %) of the total weight of the first and second ethylene copolymers. In an embodiment of the disclosure, the first ethylene copolymer comprises from about 30 to about 60 weight percent (wt %) of the total weight of the first and second ethylene copolymers. In an embodiment of the disclosure, the first ethylene copolymer comprises from about 40 to about 50 weight percent (wt %) of the total weight of the first and second ethylene copolymers.

The Second Ethylene Copolymer

In an embodiment of the disclosure, the second ethylene copolymer of the high density polyethylene composition has a density below 0.967 g/cm$^3$ but which is higher than the density of the first ethylene copolymer; a melt index $I_2$, of from about 50 to 10,000 g/10 min; a molecular weight distribution, $M_w/M_n$, of below about 3.0 and a weight average molecular weight $M_w$ that is less than the $M_w$ of the first ethylene copolymer. In one embodiment, the weight average molecular weight, $M_w$ of the second ethylene copolymer will be below 45,000 g/mole.

In an embodiment of the disclosure, the second ethylene copolymer is made with a single site catalyst, such as for example a phosphinimine catalyst.

The comonomer content in the second ethylene copolymer can be from about 0.05 to about 3 mol % as measured by $^{13}$C NMR, or FTIR or GPC-FTIR methods, or as calculated from a reactor model (see Examples section). The comonomer is one or more suitable alpha olefins, which include, but are not limited to, 1-butene, 1-hexene, 1-octene and the like. In one embodiment the alpha olefin is 1-octene.

The short chain branching in the second ethylene copolymer can be from about 0.25 to about 15 short chain branches per thousand carbon atoms (SCB1/1000Cs). In further embodiments of the disclosure, the short chain branching in the first ethylene copolymer can be from 0.25 to 10, or from 0.25 to 7.5, or from 0.25 to 5, or from 0.25 to 3 branches per thousand carbon atoms (SCB1/1000Cs). The short chain branching is the branching due to the presence of alpha-olefin comonomer in the ethylene copolymer and will for example have two carbon atoms for a 1-butene comonomer, or four carbon atoms for a 1-hexene comonomer, or six carbon atoms for a 1-octene comonomer, etc. The comonomer is one or more suitable alpha olefin. Examples of alpha olefins include, but are not limited to 1-butene, 1-hexene, 1-octene and the like. In one embodiment the alpha olefin is 1-octene.

In an embodiment of the disclosure, the comonomer content in the second ethylene copolymer is less than the comonomer content of the first ethylene copolymer (as reported for example in mol %).

In an embodiment of the disclosure, the amount of short chain branching in the second ethylene copolymer is less than the amount of short chain branching in the first ethylene copolymer (as reported in short chain branches, SCB per thousand carbons in the polymer backbone, 1000 Cs).

In an embodiment of the present disclosure, the density of the second ethylene copolymer is greater than the density of the first ethylene copolymer.

In and embodiment of the present disclosure, the density of the second ethylene copolymer is less than 0.967 g/cm$^3$. In another embodiment of the disclosure, the density of the second ethylene copolymer is less than 0.966 g/cm$^3$. In another embodiment of the disclosure, the density of the second ethylene copolymer is less than 0.965 g/cm$^3$. In another embodiment of the disclosure, the density of the second ethylene copolymer is less than 0.964 g/cm$^3$. In an embodiment of the disclosure, the density of the second ethylene copolymer is from 0.952 to 0.967 g/cm$^3$ or can be a narrower range within this range, including all the number encompassed within these ranges.

In the present disclosure, the second ethylene copolymer has a density which is higher than the density of the first ethylene copolymer, but less than about 0.037 g/cm$^3$ higher than the density of the first ethylene copolymer. In an embodiment of the disclosure, the second ethylene copolymer has a density which is higher than the density of the first ethylene copolymer, but less than about 0.035 g/cm³ higher than the density of the first ethylene copolymer. In another embodiment of the disclosure, the second ethylene copolymer has a density which is higher than the density of the first ethylene copolymer, but less than about 0.030 g/cm³ higher than the density of the first ethylene copolymer. In still another embodiment of the disclosure, the second ethylene copolymer has a density which is higher than the density of the first ethylene copolymer, but less than about 0.027 g/cm³ higher than the density of the first ethylene copolymer. In still another embodiment of the disclosure, the second ethylene copolymer has a density which is higher than the density of the first ethylene copolymer, but less than about 0.025 g/cm³ higher than the density of the first ethylene copolymer.

In an embodiment of the disclosure, the second ethylene copolymer has a weight average molecular weight $M_w$ of less than 45,000 g/mol. In another embodiment of the disclosure, the second ethylene copolymer has a weight average molecular weight $M_w$ of from about 7,500 to about 40,000. In further embodiments of the disclosure, the second ethylene copolymer has a weight average molecular weight $M_w$ of from about 9,000 to about 35,000, or from about 10,000 to about 30,000, or from about 10,000 to 25,000.

In embodiments of the disclosure, the second ethylene copolymer has a molecular weight distribution $(M_w/M_n)$ of <3.0, or ≤2.7, or <2.7, or ≤2.5, or <2.5, or ≤2.3, or from 1.8 to 2.3.

The $M_w/M_n$ value of the second ethylene copolymer can in an embodiment of the disclosure be estimated by a de-convolution of a GPC profile obtained for a bimodal polyethylene composition of which the first ethylene copolymer is a component.

In an embodiment of the disclosure, the melt index $I_2$ of the second ethylene copolymer can be from 50 to 10,000 g/10 min. In another embodiment of the disclosure, the melt index $I_2$ of the second ethylene copolymer can be from 100 to 5,000 g/10 min. In another embodiment of the disclosure, the melt index $I_2$ of the second ethylene copolymer can be from 50 to 3,500 g/10 min. In another embodiment of the disclosure, the melt index $I_2$ of the second ethylene copolymer can be from 100 to 10,000 g/10 min. In yet another embodiment of the disclosure, the melt index $I_2$ of the second ethylene copolymer can be from 1,000 to 7,000 g/10 min. In yet another embodiment of the disclosure, the melt index $I_2$ of the second ethylene copolymer can be from 1,200 to 10,000 g/10 min. In yet another embodiment of the disclosure, the melt index $I_2$ of the second ethylene copolymer can be from 1,200 to 7,000 g/10 min. In yet another embodiment of the disclosure, the melt index $I_2$ of the second ethylene copolymer can be greater than 1,200, but less than 5,000 g/10 min. In still yet another embodiment of the disclosure, the melt index $I_2$ of the second ethylene copolymer can be greater than 1,000, but less than 3,000 g/10 min. In still yet another embodiment of the disclosure, the melt index $I_2$ of the second ethylene copolymer can be greater than 500, but less than 3,000 g/10 min. In still yet another embodiment of the disclosure, the melt index $I_2$ of the second ethylene copolymer can be greater than 250, but less than 2,700 g/10 min. In still yet another embodiment of the disclosure, the melt index $I_2$ of the second ethylene copolymer can be greater than 150, but less than 2,700 g/10 min.

In an embodiment of the disclosure, the melt index $I_2$ of the second ethylene copolymer is greater than 100 g/10 min. In an embodiment of the disclosure, the melt index $I_2$ of the second ethylene copolymer is greater than 200 g/10 min. In an embodiment of the disclosure, the melt index $I_2$ of the second ethylene copolymer is greater than 500 g/10 min. In an embodiment of the disclosure, the melt index $I_2$ of the second ethylene copolymer is greater than 1,000 g/10 min. In an embodiment of the disclosure, the melt index $I_2$ of the second ethylene copolymer is greater than 1,200 g/10 min. In an embodiment of the disclosure, the melt index $I_2$ of the second ethylene copolymer is greater than 1,500 g/10 min.

In an embodiment of the disclosure, the second ethylene copolymer of the high density polyethylene composition is made with a single site catalyst and has a weight average molecular weight, $M_w$, of at most 45,000; a molecular weight distribution, $M_w/M_n$, of less than 3.0 and a density higher than the density of said first ethylene copolymer, but less than 0.967 g/cm³.

In an embodiment of the disclosure, a single site catalyst which gives an ethylene copolymer having a CDBI(50) of at least about 65% by weight, or at least about 70%, or at least about 75%, or at least about 80%, or at least about 85%, during solution phase polymerization in a single reactor, is used in the preparation of the second ethylene copolymer.

In an embodiment of the present disclosure, the second ethylene copolymer has a CDBI(50) of greater than about 60% by weight, or greater than about 65%, or greater than about 70%, or greater than about 75%, or greater than about 80%, or greater than about 85%.

The second ethylene copolymer can comprise from about 90 to about 30 wt % of the total weight of the first and second ethylene copolymers. In an embodiment of the disclosure, the second ethylene copolymer comprises from about 80 to about 40 wt % of the total weight of the first and second ethylene copolymers. In an embodiment of the disclosure, the second ethylene copolymer comprises from about 75 to about 40 wt % of the total weight of the first and second ethylene copolymers. In an embodiment of the disclosure, the second ethylene copolymer comprises from about 70 to about 40 wt % of the total weight of the first and second ethylene copolymers. In an embodiment of the disclosure, the second ethylene copolymer comprises from about 60 to about 50 wt % of the total weight of the first and second ethylene copolymers.

In embodiments of the disclosure, the melt index $I_2$ of the second ethylene copolymer is at least 50 times, or at least 100 times, or at least 1,000 times the melt index $I_2$ of the first ethylene copolymer.

The High Density Polyethylene Composition

In one embodiment the high density polyethylene composition will contain a first ethylene copolymer and a second ethylene copolymer (as defined herein).

In embodiments of the disclosure, the high density polyethylene composition has a unimodal, broad unimodal, bimodal or multimodal molecular weight distribution as determined by gel permeation chromatography.

In an embodiment of the disclosure, the high density polyethylene composition that comprises a first ethylene copolymer and a second ethylene copolymer (as defined above) will have a ratio (SCB1/SCB2) of the number of short chain branches per thousand carbon atoms in the first ethylene copolymer (i.e., SCB1) to the number of short chain branches per thousand carbon atoms in the second ethylene copolymer (i.e., SCB2) of greater than 1.0 (i.e., SCB1/SCB2>1.0).

In further embodiments of the disclosure, the ratio of the short chain branching in the first ethylene copolymer (SCB1) to the short chain branching in the second ethylene copolymer (SCB2) is at least 1.25. In still another embodiment of the disclosure, the ratio of the short chain branching in the first ethylene copolymer (SCB1) to the short chain branching in the second ethylene copolymer (SCB2) is at least 1.5.

In embodiments of the disclosure, the ratio (SCB1/SCB2) of the short chain branching in the first ethylene copolymer (SCB1) to the short chain branching in the second ethylene copolymer (SCB2) will be from greater than 1.0 to about 12.0, or from greater than 1.0 to about 10, or from greater than 1.0 to about 7.0, or from greater than 1.0 to about 5.0, or from greater than 1.0 to about 3.0.

In an embodiment of the disclosure, the high density polyethylene composition is bimodal as determined by GPC.

A bimodal or multimodal high density polyethylene composition can be identified by using gel permeation chromatography (GPC). A GPC chromatograph may exhibit two or more component ethylene copolymers, where the number of component ethylene copolymers corresponds to the number of discernible peaks. One or more component ethylene copolymers may also exist as a hump, shoulder or tail relative to the molecular weight distribution of the other ethylene copolymer component. By the phrase "bimodal as determined by GPC", it is meant that in addition to a first peak, there will be a secondary peak or shoulder which represents a higher or lower molecular weight component (i.e., the molecular weight distribution, can be said to have two maxima in a molecular weight distribution curve). Alternatively, the phrase "bimodal as determined by GPC" connotes the presence of two maxima in a molecular weight distribution curve generated according to the method of ASTM D6474-99.

In an embodiment if the disclosure, the high density polyethylene composition has a density of greater than or equal to 0.950 g/cm$^3$, as measured according to ASTM D792; a melt index $I_2$, of from about 2.0 to about 22.0 g/10 min, as measured according to ASTM D1238 (when conducted at 190° C., using a 2.16 kg weight); a molecular weight distribution, $M_w/M_n$, of from about 2.0 to about 7.0, a Z-average molecular weight $M_z$, of less than about 300,000; a stress exponent of less than 1.40; and an ESCR Condition B at 100% Igepal of at least about 3 hours.

In embodiments of the disclosure, the high density polyethylene composition has a comonomer content of less than about 0.75 mol %, or less than about 0.70 mol %, or less than about 0.65 mol %, or less than about 0.60 mol %, or less than about 0.55 mol %, or less than about 0.50 mol % as measured by FTIR or $^{13}$C NMR methods, where the comonomer is one or more suitable alpha olefins, which include, but are not limited to, 1-butene, 1-hexene, 1-octene and the like. In one embodiment the alpha olefin is 1-octene.

In an embodiment of the present disclosure, the high density polyethylene composition has a density of at least 0.950 g/cm$^3$. In further embodiments of the disclosure, the high density polyethylene composition has a density of ≥0.952 g/cm$^3$, or ≥0.953 g/cm$^3$, or ≥0.955 g/cm$^3$.

In an embodiment of the disclosure, the high density polyethylene composition has a density in the range of 0.950 to 0.970 g/cm$^3$. In an embodiment of the current disclosure, the high density polyethylene composition has a density in the range of 0.950 to 0.965 g/cm$^3$.

In an embodiment of the disclosure, the high density polyethylene composition has a density in the range of 0.950 to 0.962 g/cm$^3$.

In an embodiment of the disclosure, the high density polyethylene composition has a density in the range of 0.952 to 0.960 g/cm$^3$.

In an embodiment of the disclosure, the high density polyethylene composition has a density in the range of 0.950 to 0.960 g/cm$^3$.

In an embodiment of the disclosure, the high density polyethylene composition has a density in the range of 0.950 to 0.959 g/cm$^3$.

In an embodiment of the disclosure, the high density polyethylene composition has a density in the range of 0.951 to 0.957 g/cm$^3$.

In an embodiment of the disclosure, the high density polyethylene composition has a density in the range of 0.952 to 0.957 g/cm$^3$.

In embodiments of the disclosure, the high density polyethylene composition has a melt index $I_2$, of from 2.0 to 22.0 g/10 min according to ASTM D1238 (when conducted at 190° C., using a 2.16 kg weight) and including narrower ranges within this range and all numbers encompassed by these ranges. For example, in further embodiments of the disclosure, the high density polyethylene composition has a melt index $I_2$, of greater than 2.0, but less than 22.0 g/10 min, or from greater than 3.0 to less than 20.0 g/10 min, or from 2.0 to 15.0 g/10 min, or from 3.0 to 12.5 g/10 min, or from 4.0 to 12.5 g/10 min, or from greater than 4.0 to less than 20.0 g/10 min, or from 4.5 to 10 g/10 min, or from 5.0 to 20.0 g/10 min, or from greater than 5.0 to less than 20 g/10 min, or from 3.0 to 15.0 g/10 min, or from greater than 3.0 to 15.0 g/10 min, or from 6.0 to 12.0 g/10 min, or from 6.0 to about 10.0 g/10 min, or from about 5.0 to about 12.0 g/10 min, or from more than about 5.0 to less than about 10.0 g/10 min.

In an embodiment of the disclosure, the high density polyethylene composition has a "medium load" melt index, $I_5$, of at least about 2.5 g/10 min according to ASTM D1238 (when conducted at 190° C., using a 5 kg weight). In another embodiment of the disclosure, the high density polyethylene composition has a medium load melt index, $I_5$, of greater than about 5.0 g/10 min, as measured according to ASTM D1238 (when conducted at 190° C., using a 5 kg weight). In further embodiments of the disclosure, the high density polyethylene composition has a medium load melt index, $I_5$, of at least about 10.0 g/10 min, or at least about 4.0 g/10 min. In still further embodiments of the disclosure, the high density polyethylene composition has a medium load melt index, $I_5$, of from about 5.0 to about 25.0 g/10 min, or from about 5.0 to about 20.0 g/10 min, or from about 5.0 to about 17.5 g/10 min, or from about 5.0 to about 15.0 g/10 min.

In an embodiment of the disclosure, the high density polyethylene composition has a "high load" melt index $I_{21}$ of at least about 100 g/10 min according to ASTM D1238 (when conducted at 190° C., using a 21 kg weight). In another embodiment of the disclosure, the high density polyethylene composition has a high load melt index $I_{21}$, of greater than about 150 g/10 min.

In an embodiment of the disclosure, the high density polyethylene composition has a high load melt index $I_{21}$, of from 125 to 500 g/10 min, or from 150 to 450 g/10 min, or from 150 to 400 g/10 min.

In an embodiment of the disclosure, the high density polyethylene composition has a number average molecular weight $M_n$, of below about 30,000 g/mol. In another embodiment of the disclosure, the high density polyethylene composition has a number average molecular weight $M_n$, of below about 25,000 g/mol. In yet another embodiment of the disclosure, the high density polyethylene composition has a number average molecular weight $M_n$, of below about 20,000 g/mol.

In the present disclosure, the high density polyethylene composition has a molecular weight distribution $M_w/M_n$, of from 2.0 to 7.0 or a narrower range within this range, including all the numbers encompassed within these ranges. For example, in further embodiments of the disclosure, the high density polyethylene composition has molecular weight distribution $M_w/M_n$, of from 3.0 to 7.0, or from 3.5 to 6.0, or from 3.5 to 5.5.

In an embodiment of the disclosure, the high density polyethylene composition has a Z-average molecular weight, $M_Z$, of below about 300,000 g/mole. In another embodiment of the disclosure, the high density polyethylene composition has a Z-average molecular weight, $M_Z$, of below about 250,000 g/mole. In yet another embodiment of the disclosure, the high density polyethylene composition has a Z-average molecular weight, $M_Z$, of below about 200,000 g/mole.

In embodiments of the disclosure, the high density polyethylene composition has a ratio of Z-average molecular weight to weight average molecular weight $M_Z/M_w$, of from 2.0 to 4.0, or from 2.0 to 3.75, or from 2.25 to 3.75, or from 2.50 to 3.5.

In embodiments of the disclosure, the high density polyethylene composition has a melt flow ratio defined as $I_{21}/I_2$, of from about 15 to about 50, or from about 20 to 50, or from about 22 to 50, or from about 25 to 45, or from about 30 to 45, or from about 30 to 50, or from 22 to 50, or from about 22 to less than 50.

In an embodiment of the disclosure, the high density polyethylene composition has a melt flow rate defined as $I_{21}/I_5$, of less than 25. In another embodiment of the disclosure, the high density polyethylene composition has a melt flow rate defined as $I_{21}/I_5$, of less than 20. In another embodiment of the disclosure, the high density polyethylene composition has a melt flow rate defined as $I_{21}/I_5$, of less than 15.

In an embodiment of the disclosure, the high density polyethylene composition has a shear viscosity at about $10^5$ s$^{-1}$ (240° C.) of less than about 10 (Pa·s). In further embodiments of the disclosure, the high density polyethylene composition has a shear viscosity at about $10^5$ s$^{-1}$ (240° C.) of less than 7.5 Pa·s, or less than 6.8 Pa·s. Simultaneously, the high density polyethylene composition may have a shear viscosity at about 100 s$^{-1}$ (240° C.) of less than about 600 Pa·s, a shear viscosity at about 200 s$^{-1}$ (240° C.) of less than about 500 Pa·s and a shear viscosity at about 300 s$^{-1}$ (240° C.) of less than about 400 Pa·s.

In an embodiment of the disclosure, the high density polyethylene composition has at least one type of alpha-olefin that has at least 4 carbon atoms and its content is less than about 0.75 mol % as determined by $^{13}$C NMR. In an embodiment of the disclosure, the high density polyethylene composition has at least one type of alpha-olefin that has at least 4 carbon atoms and its content is less than about 0.65 mol % as determined by $^{13}$C NMR. In an embodiment of the disclosure, the high density polyethylene composition has at least one type of alpha-olefin that has at least 4 carbon atoms and its content is less than about 0.55 mol % as determined by $^{13}$C NMR. In an embodiment of the disclosure, the high density polyethylene composition has at least one type of alpha-olefin that has at least 4 carbon atoms and its content is less than about 0.50 mol % as determined by $^{13}$C NMR. In an embodiment of the disclosure, the high density polyethylene composition has at least one type of alpha-olefin that has at least 4 carbon atoms and its content is greater than about 0.20 to less than about 0.55 mol % as determined by $^{13}$C NMR.

In an embodiment of the disclosure, the shear viscosity ratio, $SVR_{(100,100000)}$ at 240° C. of the high density polyethylene composition can be from about 50 to about 90, or can be from about 55 to about 90, or from about 55 to about 85, or from about 55 to about 75. The shear viscosity ratio $SVR_{(100,100000)}$ is determined by taking the ratio of shear viscosity at shear rate of 100 s$^{-1}$ and shear viscosity at shear rate of 100000 s$^{-1}$ as measured with a capillary rheometer at constant temperature (e.g., 240° C.), and two dies with L/D ratio of 20 and diameter of 0.06" (from about 3 to 1000 s$^{-1}$) and L/D ratio of 20 and diameter of 0.012" (from about 1000 to 100000 s$^1$) respectively.

In an embodiment of the disclosure, the high density polyethylene composition or a molded article made from the high density polyethylene composition, has an environment stress crack resistance ESCR Condition B at 100% of at least about 3 hrs, as measured according to ASTM D1693 (at 50° C. using 100% Igepal, condition B).

In an embodiment of the disclosure, the high density polyethylene composition or a molded article made from the high density polyethylene composition, has an environment stress crack resistance ESCR Condition B at 100% of at least about 3.5 hrs, as measured according to ASTM D1693 (at 50° C. using 100% Igepal, condition B).

In an embodiment of the disclosure, the high density polyethylene composition or a molded article made from the high density polyethylene composition, has an environment stress crack resistance ESCR Condition B at 100% of at least about 4.0 hours, as measured according to ASTM D1693 (at 50° C. using 100% Igepal, condition B).

In an embodiment of the disclosure, the high density polyethylene composition or a molded article made from the high density polyethylene composition, has an environment stress crack resistance ESCR Condition B at 100% of from about 3.5 to about 15 hours, as measured according to ASTM D1693 (at 50° C. using 100% Igepal, condition B).

In an embodiment of the disclosure, the high density polyethylene composition or a molded article made from the high density polyethylene composition, has an environment stress crack resistance ESCR Condition B at 100% of from about 3.5 to about 12 hours, as measured according to ASTM D1693 (at 50° C. using 100% Igepal, condition B).

In an embodiment of the disclosure, the high density polyethylene composition or a molded article made from the high density polyethylene composition has a notched Izod impact strength of at least about 40 J/m, as measured according to ASTM D256.

In embodiments of the disclosure, the high density polyethylene composition has a TD/MD shrinkage ratio (for an injection molded disk at about 48 hours post molding) of from about 0.90 to about 1.20, or from about 0.90 to about 1.15, or from about 0.95 to about 1.15, or from about 0.90 to about 1.10, or from about 0.95 to about 1.10, or from about 0.95 to about 1.05 when measured according to the Dimensional Stability Test (DST).

In embodiments of the disclosure, the high density polyethylene composition has a TD shrinkage—MD shrinkage (for an injection molded disk at about 48 hour post molding time) of from about 0.25 to about 0.25, or from about 0.20 to about 0.20, or from about 0.15 to about 0.15, or from about 0.10 to about 0.10, or from about 0.075 to about 0.075, or from about 0.05 to about 0.05, when measured according to the Dimensional Stability Test (DST).

In an embodiment of the disclosure the high density polyethylene composition of the current disclosure has a density of at least 0.950 g/cm$^3$; a melt index $I_2$, of from greater than 3.0 to less than 20.0 g/10 min and a molecular weight distribution $M_w/M_n$, of from 2.0 to 7.0.

In an embodiment of the disclosure the high density polyethylene composition of the current disclosure has a density of from 0.950 to 0.960 g/cm$^3$; a melt index $I_2$, of from greater than 3.0 to less than 20.0 g/10 min and a molecular weight distribution $M_w/M_n$, of from 2.0 to 7.0.

In an embodiment of the disclosure the high density polyethylene composition of the current disclosure has a density of from 0.950 to 0.960 g/cm$^3$; a melt index $I_2$, of from 3.0 to 12.0 g/10 min; a molecular weight distribution $M_w/M_n$, of from 2.0 to 7.0; a number average molecular weight $M_n$, of below 30,000; a shear viscosity at $10^5$ s$^{-1}$ (240° C.) of less than 10 (Pa·s), a hexane extractables of less than 0.55%, a notched Izod impact strength of more than 40 J/m, and an ESCR B at 100% of at least about 3.5 hrs.

In an embodiment of the disclosure, the high density polyethylene composition has a hexanes extractables of less than about 0.55%. In further embodiments of the disclosure, the high density polyethylene composition has a hexanes extractables of less than about 0.50%, or less than about 0.45%, or less than about 0.40%, or less than about 0.35%.

In an embodiment of the disclosure, the high density polyethylene composition has a stress exponent, defined as Log$_{10}$[I$_6$/I$_2$]/Log$_{10}$[6.48/2.16], which is ≤1.40. In further embodiments of the disclosure, the high density polyethylene composition has a stress exponent, Log$_{10}$[I$_6$/I$_2$]/Log$_{10}$[6.48/2.16] of from 1.22 to 1.40, or from 1.22 to 1.38, or from 1.24 to 1.36.

In an embodiment of the disclosure, the high density polyethylene composition has a composition distribution breadth index (CDBI(50)), as determined by temperature elution fractionation (TREF), of ≥about 60 weight percent. In further embodiments of the disclosure, the high density polyethylene composition will have a CDBI(50) of greater than about 65%, or greater than about 70%, or greater than about 75%, or greater than about 80%.

In an embodiment of the disclosure, the high density polyethylene composition has a composition distribution breadth index (CDBI(25)), as determined by temperature elution fractionation (TREF), of ≥about 55 weight percent. In further embodiments of the disclosure, the high density polyethylene composition will have a CDBI(25) of greater than about 60%, or greater than about 65%, or from about 55 to about 75%, or from about 60 to about 75%.

Optionally, additives can be added to the high density polyethylene composition. Additives can be added to the high density polyethylene composition during an extrusion or compounding step, but other suitable known methods will be apparent to a person skilled in the art. The additives can be added as is or as part of a separate polymer component (i.e., not the first or second ethylene polymers described above) added during an extrusion or compounding step. Suitable additives are known in the art and include but are not-limited to antioxidants, phosphites and phosphonites, nitrones, antacids, UV light stabilizers, UV absorbers, metal deactivators, dyes, fillers and reinforcing agents, nano-scale organic or inorganic materials, antistatic agents, lubricating agents such as calcium stearates, slip additives such as erucimide, and nucleating agents (including nucleators, pigments or any other chemicals which may provide a nucleating effect to the high density polyethylene composition). The additives that can be optionally added are typically added in amount of up to 20 weight percent (wt %).

One or more nucleating agent(s) may be introduced into the high density polyethylene composition by kneading a mixture of the polymer, usually in powder or pellet form, with the nucleating agent, which may be utilized alone or in the form of a concentrate containing further additives such as stabilizers, pigments, antistatics, UV stabilizers and fillers. It should be a material which is wetted or absorbed by the polymer, which is insoluble in the polymer and of melting point higher than that of the polymer, and it should be homogeneously dispersible in the polymer melt in as fine a form as possible (1 to 10 µm). Compounds known to have a nucleating capacity for polyolefins include salts of aliphatic monobasic or dibasic acids or arylalkyl acids, such as sodium succinate or aluminum phenylacetate; and alkali metal or aluminum salts of aromatic or alicyclic carboxylic acids such as sodium β-naphthoate. Another compound known to have nucleating capacity is sodium benzoate. The effectiveness of nucleation may be monitored microscopically by observation of the degree of reduction in size of the spherulites into which the crystallites are aggregated.

Examples of nucleating agents which are commercially available and which may be added to the high density polyethylene composition are dibenzylidene sorbital esters (such as the products sold under the trademark MILLAD® 3988 by Milliken Chemical and IRGACLEAR® by Ciba Specialty Chemicals). Further examples of nucleating agents which may added to the high density polyethylene composition include the cyclic organic structures disclosed in U.S. Pat. No. 5,981,636 (and salts thereof, such as disodium bicyclo [2.2.1]heptene dicarboxylate); the saturated versions of the structures disclosed in U.S. Pat. No. 5,981,636 (as disclosed in U.S. Pat. No. 6,465,551; Zhao et al., to Milliken); the salts of certain cyclic dicarboxylic acids having a hexahydrophtalic acid structure (or "HHPA" structure) as disclosed in U.S. Pat. No. 6,599,971 (Dotson et al., to Milliken); and phosphate esters, such as those disclosed in U.S. Pat. No. 5,342,868 and those sold under the trade names NA-11 and NA-21 by Asahi Denka Kogyo, cyclic dicarboxylates and the salts thereof, such as the divalent metal or metalloid salts, (particularly, calcium salts) of the HHPA structures disclosed in U.S. Pat. No. 6,599,971. For clarity, the HHPA structure generally comprises a ring structure with six carbon atoms in the ring and two carboxylic acid groups which are substituents on adjacent atoms of the ring structure. The other four carbon atoms in the ring may be substituted, as disclosed in U.S. Pat. No. 6,599,971. An example is 1,2-cyclohexanedi-carboxylicacid, calcium salt (CAS registry number 491589-22-1). Still further examples of nucleating agents which may added to the polyethylene composition include those disclosed in WO2015042561, WO2015042563, WO2015042562 and WO 2011050042.

Many of the above described nucleating agents may be difficult to mix with the high density polyethylene composition that is being nucleated and it is known to use dispersion aids, such as for example, zinc stearate, to mitigate this problem.

In an embodiment of the disclosure, the nucleating agents are well dispersed in the high density polyethylene composition.

In an embodiment of the disclosure, the amount of nucleating agent used is comparatively small (from 5 to 3,000 parts by million per weight (based on the weight of the high density polyethylene composition)) so it will be appreciated by those skilled in the art that some care must be taken to ensure that the nucleating agent is well dispersed. In an embodiment of the disclosure, the nucleating agent is added in finely divided form (less than 50 microns, especially less than 10 microns) to the high density polyethylene composition to facilitate mixing. This type of "physical blend" (i.e., a mixture of the nucleating agent and the resin in solid form) is generally preferable to the use of a "masterbatch" of the nucleator (where the term "masterbatch" refers to the practice of first melt mixing the additive—the nucleator, in this case—with a small amount of the high density polyethylene composition—then melt mixing the "masterbatch" with the remaining bulk of the high density polyethylene composition).

In an embodiment of the disclosure, an additive such as nucleating agent may be added to the high density polyethylene composition by way of a "masterbatch", where the term "masterbatch" refers to the practice of first melt mixing the additive (e.g., a nucleator) with a small amount of the high density polyethylene composition, followed by melt mixing the "masterbatch" with the remaining bulk of the high density polyethylene composition.

In an embodiment of the disclosure, the polymer composition further comprises a nucleating agent or a mixture of nucleating agents.

In an embodiment of the disclosure, the polymer compositions described above are used in the formation of molded articles. For example, articles formed by continuous compression molding and injection molding are contemplated. Such articles include, for example, caps, screw caps, and closures for bottles. However, a person skilled in the art will readily appreciate that the compositions described above may also be used for other applications such as, but not limited to, film, injection blow molding, blow molding and sheet extrusion applications.

The high density polyethylene composition of this disclosure can be made using any conventional blending method such as but not limited to physical blending and in-situ blending by polymerization in multi reactor systems. For example, it is possible to perform the mixing of the first ethylene copolymer with the second ethylene copolymer by molten mixing of the two preformed polymers. One embodiment uses processes in which the first and second ethylene copolymers are prepared in at least two sequential polymerization stages, however, both in-series or an in-parallel dual reactor process are contemplated for use in the current disclosure. Gas phase, slurry phase or solution phase reactor systems may be used. In one embodiment a solution phase reactor systems is used.

Mixed catalyst single reactor systems may also be employed to make the polymer compositions of the present disclosure.

In an embodiment of the current disclosure, a dual reactor solution polymerization process is used as has been described in for example U.S. Pat. No. 6,372,864 and U.S. Patent Appl. No. 20060247373A1 which are incorporated herein by reference.

Generally, the catalysts used in the current disclosure will be so called single site catalysts based on a group 4 metal having at least one cyclopentadienyl ligand. Examples of such catalysts include metallocenes, constrained geometry catalysts and phosphinimine catalysts used, for example, in combination with activators selected from methylaluminoxanes, boranes or ionic borate salts and are further described in U.S. Pat. Nos. 3,645,992; 5,324,800; 5,064,802; 5,055,438; 6,689,847; 6,114,481 and 6,063,879. Such single site catalysts are distinguished from traditional Ziegler-Natta or Phillips catalysts which are also well known in the art. In general, single site catalysts produce ethylene copolymers having a molecular weight distribution ($M_w/M_n$) of less than about 3.0 and a composition distribution breadth index CDBI(50) of greater than about 65%.

In an embodiment of the disclosure, a single site catalyst is used to make an ethylene copolymer having a CDBI(50) of at least about 65% by weight, or at least about 70%, or at least about 75%, or at least about 80%, or at least about 85%, during solution phase polymerization in a single reactor, for the preparation of each of the first and the second ethylene copolymers.

In an embodiment of the disclosure, homogeneously branched ethylene copolymers are prepared using an organometallic complex of a group 3, 4 or 5 metal that is further characterized as having a phosphinimine ligand. Such a complex, when active toward olefin polymerization, is known generally as a phosphinimine (polymerization) catalyst. Some non-limiting examples of phosphinimine catalysts can be found in U.S. Pat. Nos. 6,342,463; 6,235,672; 6,372,864; 6,984,695; 6,063,879; 6,777,509 and 6,277,931 all of which are incorporated by reference herein.

Some non-limiting examples of metallocene catalysts can be found in U.S. Pat. Nos. 4,808,561; 4,701,432; 4,937,301; 5,324,800; 5,633,394; 4,935,397; 6,002,033 and 6,489,413, which are incorporated herein by reference. Some non-limiting examples of constrained geometry catalysts can be found in U.S. Pat. Nos. 5,057,475; 5,096,867; 5,064,802; 5,132,380; 5,703,187 and 6,034,021, all of which are incorporated by reference herein in their entirety.

In an embodiment of the disclosure, use of a single site catalyst that does not produce long chain branching (LCB) is used. Hexyl (C6) branches detected by NMR are excluded from the definition of a long chain branch in the present disclosure.

Without wishing to be bound by any single theory, long chain branching can increase viscosity at low shear rates, thereby negatively impacting cycle times during the manufacture of caps and closures, such as during the process of compression molding. Long chain branching may be determined using $^{13}C$ NMR methods and may be quantitatively assessed using the method disclosed by Randall in Rev. Macromol. Chem. Phys. C29 (2 and 3), p. 285.

In an embodiment of the disclosure, the high density polyethylene composition will contain fewer than 0.3 long chain branches per 1000 carbon atoms. In another embodiment of the disclosure, the high density polyethylene composition will contain fewer than 0.01 long chain branches per 1000 carbon atoms.

In an embodiment of the disclosure, the high density polyethylene composition is prepared by contacting ethylene and at least one alpha-olefin with a polymerization catalyst under solution phase polymerization conditions in at least two polymerization reactors (for an example of solution phase polymerization conditions see for example U.S. Pat. Nos. 6,372,864 and 6,984,695 and U.S. Patent Application 20060247373A1 which are incorporated herein by reference).

In an embodiment of the disclosure, the high density polyethylene composition is prepared by contacting at least one single site polymerization catalyst system (comprising at least one single site catalyst and at least one activator) with ethylene and a least one comonomer (e.g., a C3-C8 alpha-olefin) under solution polymerization conditions in at least two polymerization reactors.

In an embodiment of the disclosure, a group 4 single site catalyst system, comprising a single site catalyst and an activator, is used in a solution phase dual reactor system to prepare a high density polyethylene composition by polymerization of ethylene in the presence of an alpha-olefin comonomer.

In an embodiment of the disclosure, a group 4 single site catalyst system, comprising a single site catalyst and an activator, is used in a solution phase dual reactor system to prepare a high density polyethylene composition by polymerization of ethylene in the presence of 1-octene.

In an embodiment of the disclosure, a group 4 phosphinimine catalyst system, comprising a phosphinimine catalyst and an activator, is used in a solution phase dual reactor system to prepare a high density polyethylene composition by polymerization of ethylene in the presence of an alpha-olefin comonomer.

In an embodiment of the disclosure, a group 4 phosphinimine catalyst system, comprising a phosphinimine catalyst and an activator, is used in a solution phase dual reactor system to prepare a high density polyethylene composition by polymerization of ethylene in the presence of 1-octene.

In an embodiment of the disclosure, a solution phase dual reactor system comprises two solution phase reactors connected in series.

In an embodiment of the disclosure, a polymerization process to prepare the high density polyethylene composition comprises contacting at least one single site polymerization catalyst system (comprising at least one single site catalyst and at least one activator) with ethylene and at least one alpha-olefin comonomer under solution polymerization conditions in at least two polymerization reactors.

In an embodiment of the disclosure, a polymerization process to prepare the high density polyethylene composition comprises contacting at least one single site polymerization catalyst system with ethylene and at least one alpha-olefin comonomer under solution polymerization conditions in a first reactor and a second reactor configured in series.

In an embodiment of the disclosure, a polymerization process to prepare the high density polyethylene composition comprises contacting at least one single site polymerization catalyst system with ethylene and at least one alpha-olefin comonomer under solution polymerization conditions in a first reactor and a second reactor configured in series, with the at least one alpha-olefin comonomer being fed exclusively to the first reactor.

In one embodiment, the production of the high density polyethylene composition of the present disclosure may include an extrusion or compounding step. Such steps are well known in the art.

In one embodiment, the high density polyethylene composition can comprise further polymer components in addition to the first and second ethylene polymers. Such polymer components include polymers made in situ or polymers added to the polymer composition during an extrusion or compounding step.

In an embodiment of the disclosure, the polymer compositions described above are used in the formation of molded articles. For example, articles formed by continuous compression molding and injection molding are contemplated. Such articles include, for example, caps, screw caps, and closures for bottles.

In an embodiment of the disclosure, the closure made is a PCO 1881 CSD closure, having a weight of about 2.15 grams and having the following dimensions: Closure height (not including Tamper Ring)=about 10.7 mm; Closure height with Tamper Ring=about 15.4 mm; Outside diameter @ 4 mm=about 29.6 mm; Thread diameter=about 25.5 mm; Bump seal diameter=about 24.5 mm; Bump seal thickness=about 0.7 mm; Bump seal height to center of olive=about 1.5 mm; Bore seal diameter=about 22.5 mm; Bore seal thickness=about 0.9 mm; Bore height to center of olive=about 1.6 mm; Top panel thickness=about 1.2 mm; Tamper band undercut diameter=about 26.3 mm; Thread depth=about 1.1 mm; Thread pitch=about 2.5 mm; Thread Root @ 4 mm=27.4 mm.

In an embodiment of the disclosure, the closure is made using an injection molding process to prepare a PCO 1881 CSD closure, having a weight of about 2.15 grams and having the following dimensions: Closure height (not including Tamper Ring)=about 10.7 mm; Closure height with Tamper Ring=about 15.4 mm; Outside diameter @ 4 mm=about 29.6 mm; Thread diameter=about 25.5 mm; Bump seal diameter=about 24.5 mm; Bump seal thickness=about 0.7 mm; Bump seal height to center of olive=about 1.5 mm; Bore seal diameter=about 22.5 mm; Bore seal thickness=about 0.9 mm; Bore height to center of olive=about 1.6 mm; Top panel thickness=about 1.2 mm; Tamper band undercut diameter=about 26.3 mm; Thread depth=about 1.1 mm; Thread pitch=about 2.5 mm; Thread Root @ 4 mm=27.4 mm.

In an embodiment of the disclosure, the closure is made using a continuous compression molding process to prepare a PCO 1881 CSD closure, having a weight of about 2.15 grams and having the following dimensions: Closure height (not including Tamper Ring)=about 10.7 mm; Closure height with Tamper Ring=about 15.4 mm; Outside diameter @ 4 mm=about 29.6 mm; Thread diameter=about 25.5 mm; Bump seal diameter=about 24.5 mm; Bump seal thickness=about 0.7 mm; Bump seal height to center of olive=about 1.5 mm; Bore seal diameter=about 22.5 mm; Bore seal thickness=about 0.9 mm; Bore height to center of olive=about 1.6 mm; Top panel thickness=about 1.2 mm; Tamper band undercut diameter=about 26.3 mm; Thread depth=about 1.1 mm; Thread pitch=about 2.5 mm; Thread Root @ 4 mm=27.4 mm.

The disclosure is further illustrated by the following non-limiting examples.

EXAMPLES

General Polymer Characterization Methods

Melt indexes, $I_2$, $I_5$, $I_6$ and $I_{21}$ for the high density polyethylene composition were measured according to ASTM D1238 (when conducted at 190° C., using a 2.16 kg, a 5 Kg, a 6.48 kg and a 21 kg weight respectively).

$M_n$, $M_w$, and $M_z$ (g/mol) were determined by high temperature Gel Permeation Chromatography with differential refractive index detection using universal calibration (e.g. ASTM-D6474-99). GPC data was obtained using an instrument sold under the trade name "Waters 150c", with 1,2,4-trichlorobenzene as the mobile phase at 140° C. The samples were prepared by dissolving the polymer in this solvent and were run without filtration. Molecular weights are expressed as polyethylene equivalents with a relative standard deviation of 2.9% for the number average molecular weight ("Mn") and 5.0% for the weight average molecular weight ("Mw"). The molecular weight distribution (MWD) is the weight average molecular weight divided by the number average molecular weight, $M_w/M_n$. The z-average molecular weight distribution is $M_z/M_n$. Polymer sample solutions (1 to 2 mg/mL) were prepared by heating the polymer in 1,2,4-trichlorobenzene (TCB) and rotating on a wheel for 4 hours at 150° C. in an oven. The antioxidant 2,6-di-tert-butyl-4-methylphenol (BHT) was added to the mixture in order to stabilize the polymer against oxidative degradation. The BHT concentration was 250 ppm. Sample solutions were chromatographed at 140° C. on a PL 220 high-temperature chromatography unit equipped with four Shodex columns (HT803, HT804, HT805 and HT806) using TCB as the mobile phase with a flow rate of 1.0 mL/minute, with a differential refractive index (DRI) as the concentration detector. BHT was added to the mobile phase at a concentration of 250 ppm to protect the columns from oxidative degradation. The sample injection volume was 200 mL. The raw data were processed with Cirrus GPC software. The columns were calibrated with narrow distribution polystyrene standards. The polystyrene molecular weights were converted to polyethylene molecular weights using the Mark-Houwink equation, as described in the ASTM standard test method D6474.

Primary melting peak (° C.), heat of fusion (J/g) and crystallinity (%) was determined using differential scanning calorimetry (DSC) as follows: the instrument was first calibrated with indium; after the calibration, a polymer specimen is equilibrated at 0° C. and then the temperature was increased to 200° C. at a heating rate of 10° C./min; the melt was then kept isothermally at 200° C. for five minutes; the melt was then cooled to 0° C. at a cooling rate of 10° C./min and kept at 0° C. for five minutes; the specimen was then heated to 200° C. at a heating rate of 10° C./min. The DSC Tm, heat of fusion and crystallinity are reported from the $2^{nd}$ heating cycle.

The short chain branch frequency (SCB per 1000 carbon atoms) of the high density polyethylene composition was determined by Fourier Transform Infrared Spectroscopy (FTIR) as per the ASTM D6645-01 method. A Thermo-Nicolet 750 Magna-IR Spectrophotometer equipped with OMNIC version 7.2a software was used for the measurements. Unsaturations in the high density polyethylene composition were also determined by Fourier Transform Infrared Spectroscopy (FTIR) as per ASTM D3124-98. Comonomer content can also be measured using $^{13}C$ NMR techniques as discussed in Randall, Rev. Macromol. Chem. Phys., C29 (2&3), p 285; U.S. Pat. No. 5,292,845 and WO 2005/121239.

Polyethylene composition density (g/cm$^3$) was measured according to ASTM D792.

Hexane extractables were determined according to ASTM D5227.

Shear viscosity was measured by using a Kayeness WinKARS Capillary Rheometer (model # D5052M-115). For the shear viscosity at lower shear rates, a die having a die diameter of 0.06 inch and L/D ratio of 20 and an entrance angle of 180 degrees was used. For the shear viscosity at higher shear rates, a die having a die diameter of 0.012 inch and L/D ratio of 20 was used.

To determine $CDBI_{50}$, a solubility distribution curve is first generated for the polyethylene composition. This is accomplished using data acquired from the TREF technique. This solubility distribution curve is a plot of the weight fraction of the copolymer that is solubilized as a function of temperature. This is converted to a cumulative distribution curve of weight fraction versus comonomer content, from which the $CDBI_{50}$ is determined by establishing the weight percentage of a copolymer sample that has a comonomer content within 50% of the median comonomer content on each side of the median (See WO 93/03093 and U.S. Pat. No. 5,376,439). The $CDBI_{25}$ is determined by establishing the weight percentage of a copolymer sample that has a comonomer content within 25% of the median comonomer content on each side of the median.

The specific temperature rising elution fractionation (TREF) method used herein was as follows. Polymer samples (50 to 150 mg) were introduced into the reactor vessel of a crystallization-TREF unit (Polymer ChAR®). The reactor vessel was filled with 20 to 40 ml 1,2-trichlorobenzene (TCB), and heated to the desired dissolution temperature (e.g., 150° C.) for 1 to 3 hours. The solution (0.5 to 1.5 ml) was then loaded into the TREF column filled with stainless steel beads. After equilibration at a given stabilization temperature (e.g., 110° C.) for 30 to 45 minutes, the polymer solution was allowed to crystallize with a temperature drop from the stabilization temperature to 30° C. (0.1 or 0.2° C./minute). After equilibrating at 30° C. for 30 minutes, the crystallized sample was eluted with TCB (0.5 or 0.75 mL/minute) with a temperature ramp from 30° C. to the stabilization temperature (0.25 or 1.0° C./minute). The TREF column was cleaned at the end of the run for 30 minutes at the dissolution temperature. The data were processed using Polymer ChAR software, Excel spreadsheet and TREF software developed in-house.

High temperature GPC equipped with an online FTIR detector (GPC-FTIR) was used to measure the comonomer content as the function of molecular weight.

Plaques molded from the polyethylene compositions were tested according to the following ASTM methods: Bent Strip Environmental Stress Crack Resistance (ESCR) at Condition B at 10% IGEPAL at 50° C. and Condition B at 100% IGEPAL at 50° C., ASTM D1693; notched Izod impact properties, ASTM D256; Flexural Properties, ASTM D 790; Tensile properties, ASTM D 638; Vicat softening point, ASTM D 1525; Heat deflection temperature, ASTM D 648.

Dimensional Stability Test (DST):

The dimensional stability of the polyethylene compositions was determined as follows: A 150-ton×12-Oz Cincinnati Milacron injection molding machine (Hydradamp 150T 12 oz PC-111, serial #4001 A21/79-38) with a 2 inch (50.8 mm) screw was used to produce parts according to the conditions listed in Table 1. The mold was an ASTM test mold, which makes tensile test specimens with an overall length of 1.30 inches, an overall width of 0.75 inch, and a thickness of 0.12 inch; tensile test specimens with an overall length of 1.375 inch, an overall width of 0.375 inch, and a thickness of 0.12 inch; tensile test specimens with an overall length of 2.5 inch, an overall width of 0.375 inch, and a thickness of 0.12 inch; flexural modulus bars with a length of 5 inch, a width of 0.50 inch, and a thickness of either 0.12 inch or 0.75 inch, and an impact round disk with a diameter of 2 inch and a thickness of 0.12 inch. Immediately after molding, the injection-molded disk was removed from the runner (note: an injection molded disk with a 2 inch diameter and a thickness of 0.12 inches was used for measurements in the present invention). The diameters in both the machine (or in-flow) direction (MD) and transverse-flow direction (TD) are then measured at room temperature (23±2° C.) after 1, 24 and 48 hours of molding. Shrinkage at time t is defined as the percentage change in dimension at measurement time from the original mold dimensions:

Shrinkage percent=(Mold dimension−Specimen dimension at time $t$)×100/Mold dimension Thus, MD shrinkage is the shrinkage measured on the disk in the flow direction, and Transverse direction (TD) shrinkage is the shrinkage measured in the cross-flow direction. Here, the isotropic shrinkage is defined as the equal shrinkage in both the flow direction (in-flow) and the transverse direction. Differential shrinkage is defined as TD shrinkage minus MD shrinkage (an indication of part planarity or flatness or the extent of part warpage). The smaller the difference it is, the better the part planarity. A TD/MD shrinkage ratio, the TD shrinkage divided by MD shrinkage, can also be used as a measure of the extent of isotropic shrinkage (the closer to unity it is, the better the part planarity). The molding parameters used are summarized in Table A.

TABLE A

| Barrel Temperature (° C.), feed Section | 215.5 |
|---|---|
| Barrel Temperature (° C.), Trans. Section | 237.8 |
| Barrel Temperature (° C.), Metering Section | 237.8 |
| Barrel Temperature (° C.), Nozzle | 237.8 |
| Injection Time - High (s) | 6 |
| Injection Time - Low (s) | 23 |
| Cooling Time (s) | 30 |
| Decompression Time (s) | 0.07 |
| Clamp Open Time (s) | 0.02 |
| Mold Close Time (s) | 60 |
| Cycle Time (s) | 62 |
| Screw Speed (rpm) | 20 |
| Injection rate | Max |
| Shot size (inch) | 1.5 |
| Cushion (inch) | 0.2 |
| Injection Pressure - High (psi) | 5250 |
| Injection Pressure - Low (psi) | 5000 |
| Back Pressure (psi) | 1000 |
| Clamp Pressure - High (psi) | 1850 |
| Clamp Pressure - Low (psi) | 1000 |
| Mold Temperature (° C.), represented by cooling water | 11.7 |
| Cycle | Auto |

Copolymerization Reactor Modeling

For multicomponent (or bimodal resins) polyethylene polymers with very low comonomer content, it can be difficult to reliably estimate the short chain branching (and subsequently polyethylene resin density by combining other information) of each polymer component by mathematical deconvolution of GPC-FTIR data, as was done in, for example, U.S. Pat. No. 8,022,143. Instead, the $M_w$, $M_n$, $M_z$, $M_w/M_n$ and the short chain branching per thousand carbons (SCB/1000C) of the first and second copolymers were calculated herein, by using a reactor model simulation using the input conditions which were employed for actual pilot scale run conditions (for references on relevant reactor modeling methods, see "Copolymerization" by A. Hamielec, J. MacGregor, and A. Penlidis in *Comprehensive Polymer Science and Supplements*, volume 3, Chapter 2, page 17, Elsevier, 1996 and "Copolymerization of Olefins in a Series of Continuous Stirred-Tank Slurry-Reactors using Heterogeneous Ziegler-Natta and Metallocene Catalysts. I. General Dynamic Mathemacial Model" by J. B. P Soares and A. E Hamielec in *Polymer Reaction Engineering*, 4(2&3), p 153, 1996.) This type of model is considered reliable for the estimate of comonomer (e.g., 1-octene) content even at low comonomer incorporation levels, since the ethylene conversion, ethylene input flow and comonomer input flow can be obtained directly from the experimental conditions and because the reactive ratio (see below) can be reliably estimated for the catalyst system used in the present invention. For clarity, the "monomer" or "monomer 1" represent ethylene, while the terms "comonomer" or "monomer 2", represent 1-octene.

The model takes for input the flow of several reactive species (e.g. catalyst, monomer such as ethylene, comonomer such as 1-octene, hydrogen, and solvent) going to each reactor, the temperature (in each reactor), and the conversion of monomer (in each reactor), and calculates the polymer properties (of the polymer made in each reactor, i.e., the first and second ethylene copolymers) using a terminal kinetic model for continuously stirred tank reactors (CSTRs) connected in series. The "terminal kinetic model" assumes that the kinetics depend upon the monomer unit within the polymer chain on which the active catalyst site is located (see "Copolymerization" by A. Hamielec, J. MacGregor, and A. Penlidis in *Comprehensive Polymer Science and Supplements*, Volume 3, Chapter 2, page 17, Elsevier, 1996). In the model, the copolymer chains are assumed to be of reasonably large molecular weight to ensure that the statistics of monomer/comonomer unit insertion at the active catalyst center is valid and that monomers/comonomers consumed in routes other than propagation are negligible. This is known as the "long chain" approximation.

The terminal kinetic model for polymerization includes reaction rate equations for activation, initiation, propagation, chain transfer, and deactivation pathways. This model solves the steady-state conservation equations (e.g., the total mass balance and heat balance) for the reactive fluid which comprises the reactive species identified above.

The total mass balance for a generic CSTR with a given number of inlets and outlets is given by:

$$0 = \Sigma_i \dot{m}_i \tag{1}$$

where $\dot{m}_i$ represents the mass flow rate of individual streams with index i indicating the inlet and outlet streams.

Equation (1) can be further expanded to show the individual species and reactions:

$$0 = \frac{\sum_i^{m\dot{x}_{ij}} / M_i}{\rho_{mix} V} + R_j / \rho_{mix} \tag{2}$$

where $M_i$ is the average molar weight of the fluid inlet or outlet (i), $x_{ij}$ is the mass fraction of species j in stream i, $\rho_{mix}$ is the molar density of the reactor mixture, V is the reactor volume, $R_j$ is the reaction rate for species j, which has units of kmol/m³ s.

The total heat balance is solved for an adiabatic reactor and is given by:

$$0 = (\Sigma \dot{m}_i \Delta H_i + q_{Rx} V + \dot{W} - \dot{Q}) \tag{3}$$

where, $\dot{m}_i$ is the mass flow rate of stream i (inlet or outlet), $\Delta H_i$ is the difference in enthalpy of stream i versus a reference state, $q_{Rx}$ is the heat released by reaction(s), V is the reactor volume, $\dot{W}$ is the work input (i.e., agitator), $\dot{Q}$ is the heat input/loss.

The catalyst concentration input to each reactor is adjusted to match the experimentally determined ethylene conversion and reactor temperature values in order solve the equations of the kinetic model (e.g., propagation rates, heat balance and mass balance).

The $H_2$ concentration input to each reactor may be likewise adjusted so that the calculated molecular weight distribution of a polymer made over both reactors (and, hence, the molecular weight of polymer made in each reactor) matches that which is observed experimentally.

The degree of polymerization (DPN) for a polymerization reaction is given by the ratio of the rate of chain propagation reactions over the rate of chain transfer/termination reactions:

$$DPN = \frac{k_{p11}\phi_1[m_1] + k_{p12}\phi_1[m_2] + k_{p21}\phi_2[m_2]}{k_{tm11}[m_1]\phi_1 + k_{tm12}[m_2]\phi_1 + k_{tm21}[m_2]\phi_2 + k_{ts1}\phi_1 + k_{ts2}\phi_2 + k_{tH1}[H] + k_{tH2}[H]} \tag{4}$$

where $k_{p12}$ is the propagation rate constant for adding monomer 2 to a growing polymer chain ending with monomer 1, $[m_1]$ is the molar concentration of monomer 1

(ethylene) in the reactor, [m$_2$] is the molar concentration of monomer 2 (1-octene) in the reactor, k$_{tm12}$ the termination rate constant for chain transfer to monomer 2 for a growing chain ending with monomer 1, k$_{ts1}$ is rate constant for the spontaneous chain termination for a chain ending with monomer 1, k$_{tH1}$ is the rate constant for the chain termination by hydrogen for a chain ending with monomer 1. $\phi_1$ and $\phi_2$ and the fraction of catalyst sites occupied by a chain ending with monomer 1 or monomer 2 respectively.

The number average molecular weight (Mn) for a polymer follows from the degree of polymerization and the molecular weight of a monomer unit. From the number average molecular weight of polymer in each reactor, and assuming a Flory distribution for a single site catalyst, the molecular weight distribution is determined for the polymer formed in each reactor:

$$w(n) = \tau^2 n e^{-\tau n} \quad (5)$$

where $$\tau = \frac{1}{DPN},$$

and w(n) is the weight fraction of polymer having a chain length n.

The Flory distribution can be transformed into the common log scaled GPC trace by applying:

$$\frac{dW}{d\log(M)} = \ln(10) \frac{n^2}{DPN^2} e^{\left(-\frac{n}{DPN}\right)} \quad (6)$$

where $$\frac{dW}{d\log(MW)}$$

is the differential weight fraction of polymer with a chain length n (n=MW/28 where 28 is the molecular weight of the polymer segment corresponding to a C$_2$H$_4$ unit) and DPN is the degree of polymerization as calculated by Equation (4). From the Flory model, the M$_w$ and the M$_z$ of the polymer made in each reactor are: M$_w$=2×M$_n$ and M$_z$=1.5×M$_w$.

The overall molecular weight distribution over both reactors is simply the sum of the molecular weight distribution of polymer made in each reactor, and where each Flory distribution is multiplied by the weight fraction of polymer made in each reactor:

$$\frac{d\overline{W}}{d\log(MW)} = \quad (7)$$

$$w_{R1}\left(\ln(10)\frac{n^2}{DPN_{R1}^2}e^{\left(-\frac{n}{DPN_{R1}}\right)}\right) + w_{R2}\left(\ln(10)\frac{n^2}{DPN_{R2}^2}e^{\left(-\frac{n}{DPN_{R2}}\right)}\right)$$

where $\overline{dW}/d\log(MW)$ is the overall molecular weight distribution function, w$_{R1}$ and w$_{R2}$ are the weight fraction of polymer made in each reactor, DPN$_1$ and DPN$_2$ is the average chain length of the polymer made in each reactor (i.e. DPN$_1$=M$_{nR1}$/28). The weight fraction of material made in each reactor is determined from knowing the mass flow of monomer and comonomer into each reactor along with knowing the conversions for monomer and comonomer in each reactor.

The moments of the overall molecular weight distribution (or the molecular weight distribution of polymer made in each reactor) can be calculated using equations 8a, 8b and 8c (a Flory Model is assumed above, but the below generic formula apply to other model distributions as well):

$$\overline{M_n} = \frac{\sum_i w_i}{\sum_i \frac{w_i}{M_i}} \quad (8a)$$

$$\overline{M_w} = \frac{\sum_i w_i M_i}{\sum_i w_i} \quad (8b)$$

$$\overline{M_z} = \frac{\sum_i w_i M_i^2}{\sum_i w_i M_i} \quad (8c)$$

The comonomer content in the polymer product (in each reactor) may also be calculated using the terminal kinetic model and long chain approximations discussed above (see A. Hamielec, J. MacGregor, and A. Penlidis. Comprehensive Polymer Science and Supplements, Volume 3, Chapter: Copolymerization, page 17, Elsevier, 1996).

For a given catalyst system, the comonomer (e.g., 1-octene) incorporation is a function of the monomer (e.g., ethylene) conversion, the comonomer to monomer ratio in the reactor ($\gamma$) and the reactivity ratio of monomer 1 (e.g., ethylene) over monomer 2 (e.g., 1-octene):

$$r_1 = k_{p11}/k_{p12}.$$

For a CSTR, the molar ratio of ethylene to comonomer in the polymer (Y) can be estimated knowing the reactivity ratio r$_1$ of the catalyst system and knowing the ethylene conversion in the reactor (Q$_{m1}$). A quadratic equation can be derived using the May and Lewis equation for instantaneous comonomer incorporation (see "Copolymerization" by A. Hamielec, J. MacGregor, and A. Penlidis in *Comprehensive Polymer Science and Supplements*, Volume 3, Chapter 2, page 17, Elsevier, 1996) and solving the mass balance around the reaction. The molar ratio of ethylene to 1-octene in the polymer is the negative root of the following quadratic equation:

$$-Y^2\gamma/4 + [r_1 + Q_{m1}(1-r_1) + \gamma/4]Y - Q_{m1} = 0 \quad (9)$$

where Y is the molar ratio of ethylene to 1-octene in the polymer, $\gamma$ is the mass flow ratio of 1-octene to ethylene going the reactor, r$_1$ is the reactivity ratio of monomer 1 to monomer 2 for the catalyst system (r$_1$=k$_{p11}$/k$_{p12}$) and Q$_{m1}$ is the ethylene monomer fractional conversion.

The branching frequency can then be calculated knowing the molar ratio of monomer 1 to monomer 2 in the polymer:

$$BF = \frac{500}{Y+1} \quad (10)$$

where Y, is the molar ratio of monomer 1 (ethylene) over monomer 2 (1-octene) in the polymer, and BF is the branching frequency (branches per 1000 carbon atoms).

The overall branching frequency distribution (BFD) of the ethylene composition can be calculated by knowing the molecular weight distribution and weight fraction of polymer made in each reactor, and the average branching frequency (BF) of the ethylene copolymer made in each reactor. The fraction of polymer made in each reactor can be calculated from the experimental mass flows and conversion of monomer and comonomer in each reactor. The branching frequency distribution function is obtained by calculating the average branch content for each molecular weight value of the overall molecular weight distribution function made from the two Flory distributions:

$$BF_{MW} = \frac{w_{R1}BF_{R1}F_1(MW_{R1}) + w_{R2}BF_{R2}F_2(MW_{R2})}{w_{R1}F_1(MW_{R1}) + w_{R2}F_2(MW_{R2})} \quad (11)$$

where $BF_{MW}$ is the branching at molecular weight (MW), $w_{R1}$ and $w_{R2}$ are the weight fraction of polymer made in Reactor 1 and Reactor 2, $BF_{R1}$ and $BF_{R2}$ are the average branching frequency of polymer made in R1 and R2 (from Equations 9 and 10), $F_1(MW_{R1})$ and $F_2(MW_{R2})$ are Flory distribution function from Reactor 1 and Reactor 2.

The overall branching frequency of the polyethylene composition is given by the weighted average of the branching frequency of the polymer made in each reactor:

$$BF_{avg} = w_1 BF_1 + w_2 BF_2 \quad (12)$$

where, $BF_{avg}$ is the average branching frequency for the total polymer (e.g. the polyethylene composition), $w_1$ and $w_2$ are the weight fraction of material made in each reactor, $BF_1$ and $BF_2$ are the branching frequency of material made in each reactor (e.g., the branching frequency of the first and second ethylene copolymers).

For the polymer obtained in each reactor, the key resin parameters which are obtained from the above described kinetic model are the molecular weights Mn, Mw and Mz, the molecular weight distributions $M_w/M_n$ and Mz/Mw and the branching frequency (SCB/1000 Cs). With this information in hand, a component (or composition) density model and a component (or composition) melt index, $I_2$, model was used according to the following equations, which were empirically determined, to calculate the density and melt index $I_2$ of each of the first and second ethylene copolymers:

Density:

$$\frac{1}{\rho} = 1.0142 + 0.0033(1.22 \cdot BF)^{0.8346} + \frac{0.0303 k^{0.9804}}{1 + \frac{0.3712}{e^{1.22BF}}}$$

where, BF is the branching frequency, $k = \text{Log}_{10}(M_n/1000)$

Melt Index, $I_2$ (MI):

$$\text{Log}_{10}(MI) = 7.8998 - 3.9089 \text{Log}_{10}\left(\frac{M_w}{1000}\right) - 0.2799 \frac{M_n}{M_w}$$

Hence, the above models were used to estimate the branch frequency, weight fraction (or weight percent), melt index ($I_2$) and the density of the polyethylene composition components, which were formed in each of reactor 1 and 2 (i.e. the first and second ethylene copolymers).

Closures

Generally, the mechanically sealing surfaces between a polyethylene closure and PET bottle neck finish have very complex geometries. As such it is difficult to perform a systematic study using general experimental methods. For example, numerical simulations (e.g., Finite Element Analysis) may be useful for this purpose, but the inputs of the material properties for this type of analysis generally use those from compression-molded plaques made in a laboratory environment. Compression molded plaques however, may have very different material morphologies and properties than those of a closure manufactured with industrial injection molding or continuous compression molding processes. A methodology which can be used to obtain closure strain model parameters on closures that have been made according to commercial practices provides an alternative. One such methodology, also used in the present disclosure, was recently disclosed at an ANTEC meeting as "*Deformation Measurement, Modeling and Morphology Study for HDPE Caps and Closures*", XiaoChuan (Alan) Wang, Mar. 23-25, 2015, Orlando, Fla., USA.

The methodology used in the present disclosure is to use the deformation (e.g., creep) of the top panel of an as-is closure to approximate that between the mechanically sealing surfaces of the plastic closure and PET bottle neck finish after a closure is put or screwed onto a PET bottle (see FIGS. 1-5 in "*Deformation Measurement, Modeling and Morphology Study for HDPE Caps and Closures*", XiaoChuan (Alan) Wang, Mar. 23-25, 2015, Orlando, Fla., USA, ANTEC meeting). The use of a closure, instead of a standardized plaque, reflects the true molded material morphology and includes the contribution of the closure design. The deformation of the top panel of the closure can be well defined for the purpose of comparing closures made from different materials. By examining the top panel of the closure, one avoids dealing with the complex geometries of the sealing surfaces.

The following measurements and modeling can be used for any "as-is" closure design, provided that the closures being compared are prepared using substantially the same method under substantially similar conditions to provide closures having substantially similar design and dimensions. By way of non-limiting example only, the following method of preparing closures, closures which can then be compared using the methods described herein, is provided.

Method of Making a Closure by Injection Molding

A Sumitomo injection molding machine and 2.15-gram PCO (plastic closure only) 1881 carbonated soft drink (CSD) closure mold was used to prepare the closures herein. A Sumitomo injection molding machine (model SE75EV C250M) having a 28 mm screw diameter was used. The 4-cavity CSD closure mold was manufactured by Z-moulds (Austria). The 2.15-gram PCO 1881 CSD closure design was developed by Universal Closures Ltd. (United Kingdom). During the closure manufacturing, four closure parameters, the diameter of the top of the cap, the bore seal diameter, the tamper band diameter and the overall cap height, were measured and ensured to be within quality-control specifications.

For red pigmented closures, resins are dry-blended with 2% slip (erucamide) master batch (Ampacet slip 101797 with the 5 wt % slip; 1000 ppm slip additive in the final resin) and 1% of red masterbatch (Ampacet PE red masterbatch LJ-206971 with 1.5 wt. % red pigment; 150 ppm red pigment in the final resin) prior to injection molding.

An International Society of Beverage Technologists (ISBT) voluntary standard test method was used to determine the closure dimensions. The test used involves the selection of a mold cavity and the measurements on at least 5 closures made from that particular cavity. At least 14 dimensional measurements were obtained from closures that were aged for at least 1 week from the date of production. The closure dimension measurements was performed using a Vision Engineering, Swift Duo dual optical and video measuring system. All measurements were taken using 10× magnification and utilizing Metlogix M video measuring system software (see MetLogix $M^3$: Digital Comparator Field of View Software, User's Guide).

Example 1 (Comparative) is a closure made from a unimodal polyethylene resin having a melt index $I_2$ of 32 g/10 min, a density of 0.951 g/cm$^3$, and a weight average molecular weight Mw/Mn of 2.88, and which is made using a Ziegler-Natta catalyst in a solution olefin polymerization process. This resin is commercially available from NOVA Chemicals Corporation as SCLAIR® 2712. A GPC profile for the resin is given in FIG. 1A.

Example 2 is a closure made from a unimodal polyethylene copolymer and has a melt index $I_2$ of 6.7 g/10 min, a density of 0.954 g/cm$^3$, and a weight average molecular weight Mw/Mn of 2.72. The unimodal polyethylene copolymer used in Example 2, was made using a Ziegler-Natta catalyst in a solution olefin polymerization process. This resin is commercially available from NOVA Chemicals Corporation as SCLAIR® 2807. A GPC profile for the resin is given in FIG. 1B.

Example 3 is a closure made from a bimodal polyethylene composition and has a melt index $I_2$ of 7.0 g/10 min, a density of 0.958 g/cm$^3$, and a weight average molecular weight Mw/Mn of 3.70. The polyethylene composition used in Example 3, was made using a single site catalyst in a solution olefin polymerization process. Further details on the polyethylene composition used in Example 3 and methods of its preparation are disclosed in U.S. Pat. No. 9,074,082, which is incorporated herein by reference in its entirety. A GPC profile for the resin is given in FIG. 1C.

The polymers used to make closures in Examples 1-3 are shown in Table 1A along with their plaque data. The data for the first and second ethylene copolymer components of Example 3 are shown in Table 1B. The closures were formed by injection molding, and the injection-molding processing conditions are given in Table 2. Closure dimensions are provided in Table 3.

TABLE 1A

Polymer Properties and Plaque Data

| | Example | | |
|---|---|---|---|
| | 1, Comp. | 2 | 3 |
| Polymer | | | |
| Modality | Unimodal | Unimodal | Bimodal |
| Alpha Olefin Comonomer | 1-butene | 1-butene | 1-octene |
| $I_2$, g/10 min | 32 | 6.7 | 7.03 |
| Density, g/cm$^3$ | 0.951 | 0.954 | 0.9581 |
| $I_{21}$, g/10 min | | | 242 |
| $I_{21}/I_2$ | 22.7 | 28.2 | 34.4 |
| Stress Exponent | 1.24 | 1.33 | 1.30 |
| Mn (g/mol) | 14928 | 26005 | 17097 |
| Mw (g/mol) | 43003 | 70836 | 63337 |
| Mz (g/mol) | 95318 | 185530 | 154296 |
| Mw/Mn | 2.88 | 2.72 | 3.70 |
| CDBI$_{50}$ (%) | 68.7 | 78.8 | 73.2 |
| CDBI$_{25}$ (%) | 50.5 | 66.9 | 60.9 |
| DSC | | | |
| Primary Melting Peak (° C.) | 126.99 | 130.04 | 131.70 |
| Heat of Fusion (J/g) | 210.4 | 215.7 | 225.5 |
| Crystallinity (%) | 72.55 | 74.37 | 77.77 |
| FTIR | | | |
| Short chain branching per 1000 carbons (uncorrected for chain end - CH$_3$) | 1.3 | <0.5 | 1.4 |

TABLE 1A-continued

Polymer Properties and Plaque Data

| | Example | | |
|---|---|---|---|
| | 1, Comp. | 2 | 3 |
| Internal unsaturation (No. per 100 carbons) | 0.008 | 0.004 | 0.005 |
| Side chain unsaturation (No. per 100 carbons) | 0.005 | 0.003 | 0.001 |
| Terminal unsaturation (No. per 100 carbons) | 0.085 | 0.072 | 0.010 |
| Plaque | | | |
| 2% secant flexural modulus (MPa) | 786 | 886 | 1209 |
| ESCR Cond. B at 10% (hrs) | 0 | 3 | 3 |
| ESCR Cond. B at 100% (hrs) | — | — | 5 |
| Heat Deflection Temp at 66 PSI (° C.) | 66 | 74 | 73.3 |
| VICAT Softening Point (° C.) | 122 | 127 | 127.8 |
| Notched Izod Impact Strength (ft-lb/in) | 0.66 | 1.13 | 1.02 |
| Hexane Extractables (wt %) | 0.43 | 0.24 | 0.22 |

TABLE 1B

Example 3, Component Properties

| First Ethylene Copolymer | |
|---|---|
| Weight fraction | 0.447 |
| Mw | 119379 |
| $I_2$ (g/10 min) | 0.44 |
| Density, d1 (g/cm$^3$) | 0.9438 |
| Comonomer | Octene |
| SCB1/1000 C | 0.44 |
| SCB1 mol % | 0.09 |
| Second Ethylene Copolymer | |
| Weight fraction | 0.553 |
| Mw | 18458 |
| $I_2$ (g/10 min) | 646 |
| Density, d2 (g/cm$^3$) | 0.9633 |
| Comonomer | Octene |
| SCB2/1000 C | 0.23 |
| SCB2 mol % | 0.05 |
| Estimated (d2 − d1), g/cm$^3$ | 0.0195 |
| Estimated SCB1/SCB2 | 1.85 |

TABLE 2

Injection Molding Processing Conditions

| | Example | | |
|---|---|---|---|
| | 1, Comp. | 2 | 3 |
| Additives (Color & Formulation) | 1% red, 2% slip (1000 ppm slip) | 1% red, 2% slip (1000 ppm slip) | 1% red, 2% slip (1000 ppm slip) |
| Part Weight - 4 cavities (g) | 8.653 | 8.61 | 8.621 |
| Injection Speed (mm/s) | 45 | 45 | 45 |
| Cycle time (s) | 3.631 | 3.616 | 3.592 |
| Filling time (s) | 0.661 | 0.672 | 0.660 |
| Dosing time (s) | 1.788 | 1.833 | 1.851 |
| Minimum Cushion (mm) | 9.758 | 9.748 | 9.651 |
| Filling peak pressure (psi) | 8294.6 | 12628.8 | 12913.9 |
| Full peak pressure (psi) | 8345 | 12653.7 | 12918.2 |

TABLE 2-continued

Injection Molding Processing Conditions

| | Example | | |
|---|---|---|---|
| | 1, Comp. | 2 | 3 |
| Hold end position (mm) | 12.144 | 12.436 | 11.9 |
| Clamp force (ton) | 17.1 | 18.9 | 19.8 |
| Fill start position (mm) | 39.461 | 34.952 | 39.422 |
| Dosing back pressure (psi) | 824.2 | 830.9 | 828.0 |
| Pack pressure (psi) | 8286.7 | 12634.3 | 12571.3 |
| Filling time 1 (s) | 0.665 | 0.676 | 0.661 |
| Temperature zone 1 (° C.) | 180 | 180 | 180 |
| Temperature zone 2 (° C.) | 185 | 185 | 185 |
| Temperature zone 3 (° C.) | 190 | 190 | 190 |
| Temperature zone 4 (° C.) | 200 | 200 | 200 |
| Temperature zone 5 (° C.) | 200 | 200 | 200 |
| Mold temperature stationary (° F.) | 58 | 58 | 58 |
| Mold temperature moving (° F.) | 58 | 58 | 58 |

TABLE 3

Closure Dimensions

| | Example | | |
|---|---|---|---|
| | 1, Comp. | 2 | 3 |
| Additives (Color & Formulation) | 1% red, 2% slip (1000 ppm slip) | 1% red, 2% slip (1000 ppm slip) | 1% red, 2% slip (1000 ppm slip) |
| Closure height no Tamper Ring (mm) | 10.67 | 10.67 | 10.67 |
| Closure height with Tamper Ring (mm) | 15.44 | 15.32 | 15.25 |
| Outside diameter @ 4 mm (mm) | 29.58 | 29.61 | 29.69 |
| Thread diameter (mm) | 25.54 | 25.56 | 25.74 |
| Bump seal diameter (mm) | 24.52 | 24.45 | 24.5 |
| Bump seal thickness (mm) | 0.68 | 0.69 | 0.71 |
| Bump seal height to center of olive (mm) | 1.52 | 1.49 | 1.52 |
| Bore seal diameter (mm) | 22.5 | 22.50 | 22.54 |
| Bore seal thickness (mm) | 0.91 | 0.93 | 0.95 |
| Bore height to center of olive (mm) | 1.58 | 1.59 | 1.58 |
| Top panel thickness (mm) | 1.21 | 1.22 | 1.22 |
| Tamper band undercut diameter (mm) | 26.29 | 26.19 | 26.71 |
| Thread depth (mm) | 1.06 | 1.05 | 1.05 |
| Thread pitch (mm) | 2.54 | 2.62 | 2.58 |
| Thread Root @ 4 mm (mm) | 27.35 | 27.37 | 27.42 |
| Cap weight (g) | 2.164 | 2.158 | 2.173 |

Deformation Analysis of Solid-State Closures

A DHR-3 rotational rheometer testing bar was modified by attaching an annular probe (see FIGS. 2A and 2B) to its end. This set up was used for the compressive deformation tests. The rheometer has a temperature chamber (oven) that allows one to measure the deformation responses at different temperatures. The annular probe made had an inner diameter of 6.4 mm and an outer diameter of 10.8 mm. The annular structure is designed to avoid contact of the probe with the center of the top panel of a closure since sometimes the gate mark (due to the nature of the injection molding process) is not completely flat (note: closures made by continuous compression molding processes will normally not have such marks at the center of the top panel of the closure). A closure holder (see FIG. 3) was also designed to hold the closure. This holder has four setting screws to fix the position of the closure inside the holder. The probe is glued to the testing bar using high temperature resistant silicone grease. The projected or contact area of the closure surface to be put under stress was 0.5944 $cm^2$. Tamper-evident rings were removed from the closures prior to testing, so that only the deformation of the top panel at the projected area was induced. The closure without tamper-evident ring is fixed in the stainless steel secure ring closure holder (see FIG. 3) and placed on the bottom plate of the rheometer. The point where the probe first touches the closure is set as the zero position. For the time sweep test, the sample was conditioned in the oven for 15 minutes at 93° C. before the testing started. A person skilled in the art will recognize that the present testing can be carried out at any suitable temperature for obtaining results, and especially any temperature above ambient to obtain results applicable to use of closures in hot fill or aseptic fill processes. An initial 2.5 N compression force was applied and then the time sweep was carried out with 1 rad/s frequency and 0.0001% radial strain for 300 seconds at 93° C. (which at such a low value does not affect axial responses; if higher radial strain were used, the solid samples might induce distortions in the axial force and deformation, ΔL data obtained). During this process, the instantaneous compressive force and deformation measured as ΔL vs. time were recorded. The compressive strain ε (taken as a positive value for modeling purposes, see below) is calculated by taking the ratio of ΔL/thickness (in mm) of the closure top panel. The stress undergone at the contact area is calculated by using the recorded force divided by the actual contact area (i.e., 0.5944 $cm^2$). The data provided in Table 4 is an example data set obtained for each closure, and came from the modified solid-state deformation analysis carried out on each closure (Time in seconds, Axial Force in Newtons, Deformation or DL in mm, Temperature in ° C. and Angular Frequency, in radians per second). The data from each closure was modeled to obtain the strain model parameters (A, n and m). The data reported in Tables 4A-4C show one set of values for the raw data obtained by the above described deformation test for each closure made of a specific resin. In practice, data were collected for 4 to 6 closures made from each resin. The data from the 4-6 closures measured for each resin type was used as the basis for modeling after converting the axial force to stress and the deformation to strain. The numbers obtained with the model (on the closure/resin systems) were then averaged and are provided below in Table 5. Without wishing to be bound by theory, it is believed that the compressive deformation resistance evaluated using the current methodology also reflects the deformation resistance under any other deformation modes, such as tensile deformation; it is further believed that the deformation of the top panel of an as-is closure approximates that which occurs between the mechanically sealing surfaces of a plastic closure and a PET bottle neck finish after a closure is secured to a PET bottle.

TABLE 4A

Example 1

| Time (s) | Force (N) | DL (mm) | Top panel thickness (mm) | Projected Area (cm$^2$) | Temperature (° C.) | Angular frequency (rad/s) | Strain | Stress (N/cm$^2$) |
|---|---|---|---|---|---|---|---|---|
| 13.1815 | 0.3748 | 0.1319 | 1.21 | 0.5944 | 93.01 | 1 | 10.9% | 0.6305 |
| 27.1430 | 0.9321 | 0.1827 | 1.21 | 0.5944 | 93 | 1 | 15.1% | 1.5681 |
| 41.2604 | 1.3460 | 0.2207 | 1.21 | 0.5944 | 93 | 1 | 18.2% | 2.2644 |
| 55.0815 | 1.6385 | 0.2480 | 1.21 | 0.5944 | 93.01 | 1 | 20.5% | 2.7566 |
| 68.9493 | 1.8469 | 0.2687 | 1.21 | 0.5944 | 93.01 | 1 | 22.2% | 3.1071 |
| 83.5972 | 2.0062 | 0.2853 | 1.21 | 0.5944 | 93.01 | 1 | 23.6% | 3.3751 |
| 97.5586 | 2.1170 | 0.2974 | 1.21 | 0.5944 | 93 | 1 | 24.6% | 3.5616 |
| 111.3953 | 2.1974 | 0.3067 | 1.21 | 0.5944 | 92.99 | 1 | 25.3% | 3.6969 |
| 125.3256 | 2.2625 | 0.3141 | 1.21 | 0.5944 | 93 | 1 | 26.0% | 3.8064 |
| 139.3807 | 2.3090 | 0.3201 | 1.21 | 0.5944 | 93 | 1 | 26.5% | 3.8846 |
| 153.4513 | 2.3473 | 0.3249 | 1.21 | 0.5944 | 93 | 1 | 26.9% | 3.9490 |
| 167.3348 | 2.3736 | 0.3288 | 1.21 | 0.5944 | 92.99 | 1 | 27.2% | 3.9933 |
| 181.2494 | 2.3928 | 0.3319 | 1.21 | 0.5944 | 93 | 1 | 27.4% | 4.0256 |
| 195.1485 | 2.4085 | 0.3347 | 1.21 | 0.5944 | 92.99 | 1 | 27.7% | 4.0520 |
| 208.9384 | 2.4204 | 0.3370 | 1.21 | 0.5944 | 93 | 1 | 27.9% | 4.0720 |
| 222.9310 | 2.4293 | 0.3391 | 1.21 | 0.5944 | 93 | 1 | 28.0% | 4.0869 |
| 237.0173 | 2.4381 | 0.3409 | 1.21 | 0.5944 | 92.99 | 1 | 28.2% | 4.1018 |
| 251.0100 | 2.4449 | 0.3425 | 1.21 | 0.5944 | 93 | 1 | 28.3% | 4.1132 |
| 264.7530 | 2.4306 | 0.3425 | 1.21 | 0.5944 | 92.99 | 1 | 28.3% | 4.0891 |
| 278.3245 | 2.4216 | 0.3425 | 1.21 | 0.5944 | 93 | 1 | 28.3% | 4.0740 |
| 292.0208 | 2.4114 | 0.3425 | 1.21 | 0.5944 | 93 | 1 | 28.3% | 4.0569 |
| 305.8886 | 2.4020 | 0.3425 | 1.21 | 0.5944 | 92.99 | 1 | 28.3% | 4.0411 |

TABLE 4B

Example 2

| Time (s) | Force (N) | DL (mm) | Top panel thickness (mm) | Projected Area (cm$^2$) | Temperature (° C.) | Angular frequency (rad/s) | Strain | Stress (N/cm$^2$) |
|---|---|---|---|---|---|---|---|---|
| 13.2907 | 0.5481 | 0.1308 | 1.22 | 0.5944 | 92.97 | 1 | 10.7% | 0.9221 |
| 27.3301 | 1.2390 | 0.1748 | 1.22 | 0.5944 | 92.99 | 1 | 14.3% | 2.0845 |
| 41.2760 | 1.6528 | 0.2036 | 1.22 | 0.5944 | 93 | 1 | 16.7% | 2.7807 |
| 55.1907 | 1.9107 | 0.2231 | 1.22 | 0.5944 | 93.01 | 1 | 18.3% | 3.2145 |
| 69.1989 | 2.0847 | 0.2369 | 1.22 | 0.5944 | 93.01 | 1 | 19.4% | 3.5072 |
| 83.0980 | 2.1998 | 0.2466 | 1.22 | 0.5944 | 93.01 | 1 | 20.2% | 3.7009 |
| 97.1687 | 2.2781 | 0.2538 | 1.22 | 0.5944 | 93.01 | 1 | 20.8% | 3.8326 |
| 111.0989 | 2.3328 | 0.2591 | 1.22 | 0.5944 | 93.02 | 1 | 21.2% | 3.9247 |
| 125.0292 | 2.3692 | 0.2633 | 1.22 | 0.5944 | 93 | 1 | 21.6% | 3.9859 |
| 138.8035 | 2.3951 | 0.2665 | 1.22 | 0.5944 | 93 | 1 | 21.8% | 4.0295 |
| 152.9677 | 2.4163 | 0.2691 | 1.22 | 0.5944 | 93 | 1 | 22.1% | 4.0651 |
| 166.9916 | 2.4314 | 0.2712 | 1.22 | 0.5944 | 92.99 | 1 | 22.2% | 4.0905 |
| 180.9374 | 2.4422 | 0.2730 | 1.22 | 0.5944 | 92.99 | 1 | 22.4% | 4.1087 |
| 194.5869 | 2.4360 | 0.2738 | 1.22 | 0.5944 | 92.98 | 1 | 22.4% | 4.0982 |
| 208.3456 | 2.4221 | 0.2738 | 1.22 | 0.5944 | 92.99 | 1 | 22.4% | 4.0748 |
| 221.9327 | 2.4082 | 0.2738 | 1.22 | 0.5944 | 92.99 | 1 | 22.4% | 4.0514 |
| 235.6757 | 2.4366 | 0.2757 | 1.22 | 0.5944 | 92.99 | 1 | 22.6% | 4.0993 |
| 249.4344 | 2.4284 | 0.2763 | 1.22 | 0.5944 | 93 | 1 | 22.6% | 4.0854 |
| 263.2399 | 2.4162 | 0.2763 | 1.22 | 0.5944 | 92.99 | 1 | 22.6% | 4.0650 |
| 276.9829 | 2.4077 | 0.2763 | 1.22 | 0.5944 | 92.99 | 1 | 22.6% | 4.0507 |
| 290.6324 | 2.4346 | 0.2783 | 1.22 | 0.5944 | 93 | 1 | 22.8% | 4.0959 |
| 304.3911 | 2.4237 | 0.2783 | 1.22 | 0.5944 | 93 | 1 | 22.8% | 4.0775 |

TABLE 4C

Example 3

| Time (s) | Force (N) | DL (mm) | Top panel thickness (mm) | Projected Area (cm$^2$) | Temperature (° C.) | Angular frequency (rad/s) | Strain | Stress (N/cm$^2$) |
|---|---|---|---|---|---|---|---|---|
| 0 | 0 | 0 | 1.22 | 0.5944 | 93 | 1 | 0 | 0 |
| 13.37249 | 0.4427 | 0.1327 | 1.22 | 0.5944 | 93 | 1 | 10.9% | 0.7448 |
| 27.47434 | 1.1392 | 0.1800 | 1.22 | 0.5944 | 92.99 | 1 | 14.8% | 1.9165 |
| 41.723 | 1.6244 | 0.2110 | 1.22 | 0.5944 | 92.99 | 1 | 17.3% | 2.7329 |
| 55.74726 | 1.9173 | 0.2310 | 1.22 | 0.5944 | 92.99 | 1 | 18.9% | 3.2256 |
| 69.72072 | 2.1009 | 0.2444 | 1.22 | 0.5944 | 92.99 | 1 | 20.0% | 3.5345 |
| 83.61978 | 2.2209 | 0.2537 | 1.22 | 0.5944 | 92.98 | 1 | 20.8% | 3.7364 |

TABLE 4C-continued

Example 3

| Time (s) | Force (N) | DL (mm) | Top panel thickness (mm) | Projected Area (cm²) | Temperature (° C.) | Angular frequency (rad/s) | Strain | Stress (N/cm²) |
|---|---|---|---|---|---|---|---|---|
| 97.61565 | 2.2992 | 0.2603 | 1.22 | 0.5944 | 92.99 | 1 | 21.3% | 3.8681 |
| 111.6395 | 2.3537 | 0.2650 | 1.22 | 0.5944 | 92.99 | 1 | 21.7% | 3.9598 |
| 125.6478 | 2.3896 | 0.2685 | 1.22 | 0.5944 | 92.99 | 1 | 22.0% | 4.0202 |
| 139.5936 | 2.4136 | 0.2712 | 1.22 | 0.5944 | 93 | 1 | 22.2% | 4.0605 |
| 153.4927 | 2.4303 | 0.2734 | 1.22 | 0.5944 | 93.01 | 1 | 22.4% | 4.0887 |
| 167.5478 | 2.4446 | 0.2751 | 1.22 | 0.5944 | 92.99 | 1 | 22.5% | 4.1128 |
| 181.4312 | 2.4263 | 0.2753 | 1.22 | 0.5944 | 93.01 | 1 | 22.6% | 4.0819 |
| 195.2523 | 2.4091 | 0.2753 | 1.22 | 0.5944 | 93 | 1 | 22.6% | 4.0531 |
| 209.1982 | 2.4276 | 0.2766 | 1.22 | 0.5944 | 93.02 | 1 | 22.7% | 4.0841 |
| 223.1128 | 2.4269 | 0.2776 | 1.22 | 0.5944 | 93.01 | 1 | 22.8% | 4.0829 |
| 236.8091 | 2.41 | 0.2776 | 1.22 | 0.5944 | 93.01 | 1 | 22.8% | 4.0546 |
| 250.4742 | 2.446 | 0.2795 | 1.22 | 0.5944 | 93 | 1 | 22.9% | 4.1150 |
| 264.1393 | 2.423 | 0.2794 | 1.22 | 0.5944 | 93.01 | 1 | 22.9% | 4.0763 |
| 277.8667 | 2.41 | 0.2794 | 1.22 | 0.5944 | 92.99 | 1 | 22.9% | 4.0545 |
| 291.4226 | 2.4367 | 0.2810 | 1.22 | 0.5944 | 93 | 1 | 23.0% | 4.0994 |
| 305.1189 | 2.424 | 0.2811 | 1.22 | 0.5944 | 92.99 | 1 | 23.0% | 4.0781 |

A person skilled in the art will recognize that any resin which is capable of being formed into a closure may be subjected to similar testing to provide inputs for use in the compressive strain model, so that two or more closures made of different polymeric material may be directly compared and contrasted with respect to their respective deformation behavior.

The Compressive Strain Model

Without wishing to be bound by any single theory, the responses collected for each closure reflect the characteristics of the resin used in each closure. However, since the instantaneous compressive deformation information is a function of both time and stress, which is a non-linear relationship or typical multivariate phenomenon, a model is employed to provide a better understanding of the polymer structure-closure property relationship. The model used here is a model that can adequately describe the closure deformation as a function of stress and time at a given temperature for each polymer-closure pairing.

The compressive strain data obtained as described above are modeled using a compressive strain model in order to compare the tendency of a polymer-closure system to deform under stress. Together with the compressive strain data, the model is a useful method to provide rapid and cost effective manner by which to predict polymer-closure pairing deformation properties.

The compressive strain is assumed to follow the mathematical form at a given temperature as shown below:

$$\varepsilon = A \times \sigma^n \times t^m$$

where $\varepsilon$ is the compressive strain; $\sigma$ is the stress in N/cm², t is the loading time in seconds, A is the model coefficient, n is the deformation stress exponent and m is the time exponent. Any software capable of performing non-linear regressions can be used to estimate the model parameters.

Figure 4:
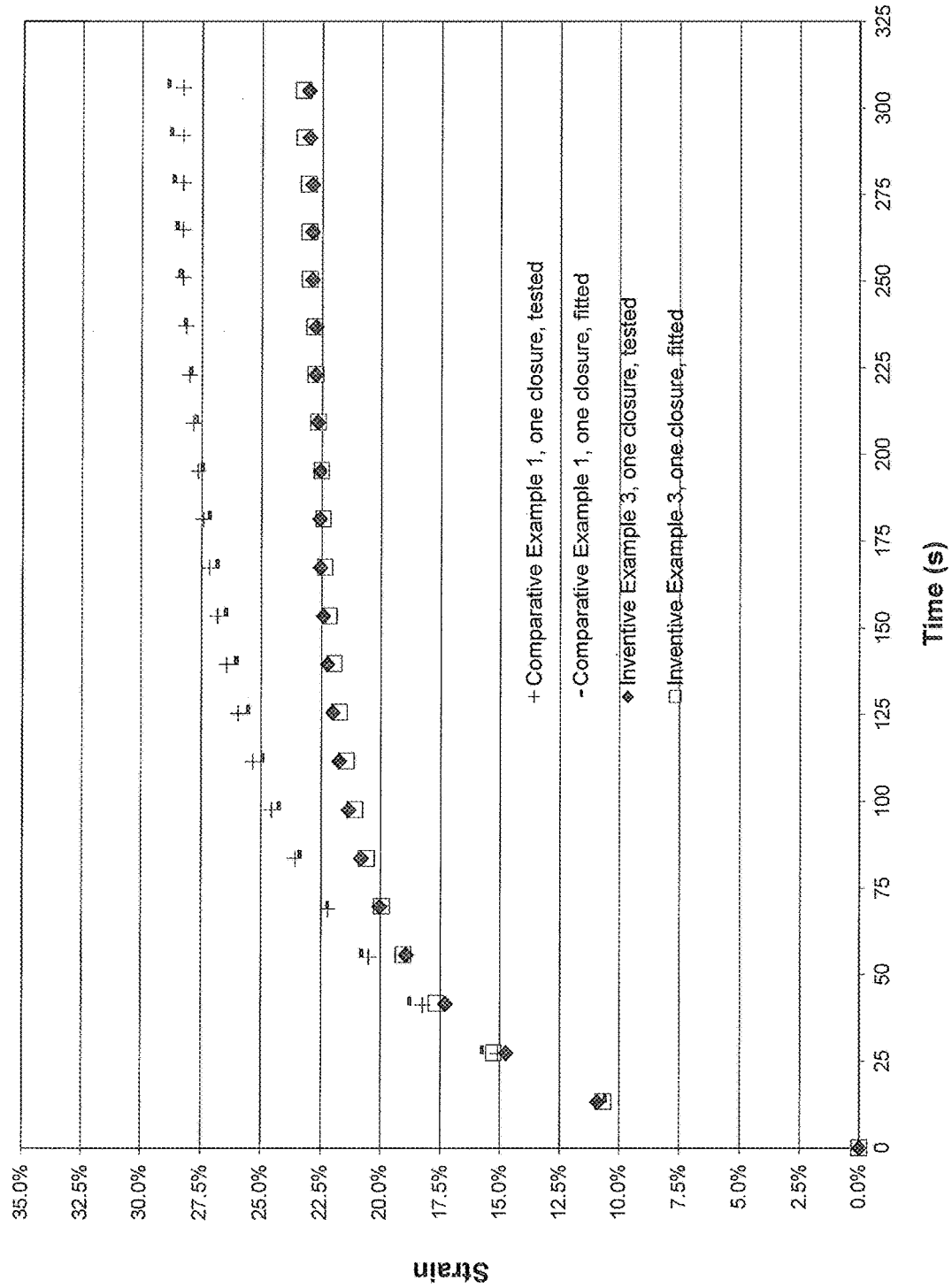
FIG. 4.

FIG. 4 shows the actual and fitted compressive strains (deformations) using the compressive strain model for Examples 1 and 3. Generally, the model fits very well with the actual deformation obtained from the closures made from the different polymer types. The average values of the fitted model parameters, A, n and m, are summarized in Table 5.

TABLE 5

Compressive Strain Model Parameters for Closures Made of Different Polyethylene Polymers

| | Example | | |
|---|---|---|---|
| | Example 1 Comparative | Example 2 | Example 3 |
| Additives (Color & Slip by Masterbatch, MB) | 1% red, 2% slip MB (1000 ppm slip) | 1% red, 2% slip (1000 ppm slip) | 1% red, 2% slip MB (1000 ppm slip) |
| Model Coefficient, A | 0.093679 | 0.091060 | 0.091720 |
| Deformation stress exponent, n | 0.348888 | 0.343505 | 0.332043 |
| Time Exponent, m | 0.115313 | 0.088631 | 0.076351 |
| Predicted creep strain at 93° C., 4 N/cm², 305 seconds; the stress is constant and creep is the deformation vs time | 29.4% | 24.3% | 22.5% |

Predicted creep strain (also shown in Table 5) is the deformation of a material at a specific time under a constant stress. Since the model described above for compressive strain fits the actual raw data very well, the model may be further used to predict the deformations under different conditions, such as increased stress levels, or predicting compressive strain at various stress values at a constant loading time.

The data provided in Table 5 clearly shows that Example 3 has a lower time exponent (m) value and better creep or deformation resistance when compared to Examples 1 and 2. The time exponent values for Example 3 is lower than 0.105. The lower the time exponent value with A and n parameters being essentially the same, the better the closure/polymer system resists deformation. As the deformation at elevated temperature is believed to be important to whether a particular polymer/closure system is suitable for a use in a hot-filling or aseptic filling process, the present model helps to establish which polyethylene resins are suitable in such end use applications.

Preparation of a Liquid Containing 4.2 Volume % $CO_2$ Sealed in a PET Container with a Closure To prepare 4.2 vol % of carbon dioxide, $CO_2$ (4.2 Gas Volume or "GV") in purified water, 10.13 grams of sodium bicarbonate ($NaHCO_3$) and 7.72 grams of citric acid ($C_6H_8O_7$) were packed into two water-soluble EVOH (ethylene vinyl alcohol) bags. Next, 600 mL of purified water was added to a PET bottle filling the bottle. Each bottle had a PCO 1881 neck finish. The bag with sodium bicarbonate and the bag with citric acid were then added to the PET bottle filled with purified water. A closure was immediately placed on the PET bottle with manual force and turned at an application angle 360°. Next the bottle-closure system was placed in a Steinfurth torque measuring machine with a proper chuck to further turn the closure at an application angle of 380° at a speed of 0.8 rpm/minute. The bottle was then shaken to ensure complete dissolution of the chemicals in water.

Elevated Temperature Cycle Test (ETCT)

This is an International Society of Beverage Technologists (ISBT) voluntary standard test. As closures may experience wide temperature swings in hot weather markets, it is essential that the closure remain on the neck finish during these temperature swings and throughout the shelf life of the product. The elevated temperature cycle test evaluates such closure performance.

After filling and capping a PET bottle with 4.2 GV of $CO_2$ as described above, the PET bottle-closure system was placed in a temperature controlled chamber. The bottle-closure system was then exposed to the following temperature program: Cycle 1; A) hold at 60° C. for 6 hours, then B) at 32° C. for 18 hours; Cycle 2; C) hold at 60° C. for six 6 hours, then D) at 32° C. for 18 hours; Cycle 3; E) hold at 60° C. for 6 hours, then F) at 32° C. for 18 hours. After each cycle component, the PET bottle-closure samples were observed for closure releases, cocked and deformed closures and leakers. A total of 24 bottle-closure systems were tested in each example. The results are shown in Table 6.

will be recognized by persons skilled in the art, that for some end use applications, including hot fill applications good performance during elevated temperature cycle test may or may not be essential.

Secure Seal Test (SST)

As PET (or glass) is more rigid than polyethylene, the deformation at the mechanically sealing surfaces of a bottle and closure package likely occurs more with the plastic closure than the bottle. Hence, it is important that the plastic closure has an appropriate deformation. Without wishing to be bound by theory, it is expected that an excessive deformation of the closure at the mechanically sealing surfaces may lead to the loss of the intimate engagement of the sealing surfaces at some point. Insufficient deformation of the closure at the mechanically sealing surfaces may not provide sufficient conformability to the shapes of the sealing surfaces on the rigid PET bottle neck finish. Appropriate deformation at the mechanically sealing surfaces can provide the intimate engagement between the sealing surfaces of the bottle (neck finish) and closure. Hence, a closure exhibiting excessive compressive strain or excessive deformation may lead to poorer sealing properties (e.g., decreased tightness) when the closure is fitted to a PET container, bottle and the like; alternatively, a closure exhibiting appropriate compressive strain or deformation may lead to improved sealing properties (e.g., improved tightness) when the closure is fitted to a PET container, bottle and the like.

The SST is an International Society of Beverage Technologists (ISBT) voluntary standard test. This test is to determine the plastic closure seal and thread integrity while under an internal pressure. A detailed description of the test follows. After filling and capping a PET bottle with 4.2 GV of $CO_2$ as described above, the PET bottle-closure system

TABLE 6[1,2]

Elevated Temperature Cycle Test of a PET Bottle - PE Closure System
(closure has additives for color, 1% red, and slip, 1000 ppm by way of 2% masterbatch)

| Example | Cycle | Cycle Half | No. of Failures | Visual Inspection Notes | % Pass (no issue) |
|---|---|---|---|---|---|
| 1, Comp. | 1 | A | No failure | | 33.3% |
| | | B | No failure | | |
| | 2 | C | 2 | Nos. 10 and 24 had visual flaws | |
| | | D | 4 | Nos. 4, 6, 7, and 21 had visual flaws | |
| | 3 | E | 3 | Nos. 12 and 20 had visual flaws; No. 11 vented gas | |
| | | F | 7 | Nos. 2 and 3 had visual flaws; Nos. 5, 14, 17, 22, and 23 vented gas | |
| 2 | 1 | A | 22 | Nos. 1, 2, 3, 4, 5, 6, 7, 9, 10, 11, 12, 13, 14, 15, 16, 17, 18, 19, 20, 22, 23, 24, tamper evident band (TEB) separated | 4% |
| | | B | No failure | | |
| | 2 | C | 1 | No. 21 tamper-evident band separated | |
| | | D | No failure | | |
| | 3 | E | No failure | | |
| | | F | No failure | | |
| 3 | 1 | A | 4 | Nos. 3, 11, 18 and 19 cracked on crown edge | 12.5% |
| | | B | 0 | Nos. 2, 4, 6, 16, 20 and 23 vented gas; 5, 12, 14 and 22 cracked on crown edge | |
| | 2 | C | 10 | | |
| | | D | 0 | Nos. 8, 9, 16 and 23 vented gas; Nos. 7, 17, and 21 cracked edge | |
| | 3 | E | 7 | | |
| | | F | 0 | No failures | |

Notes:
[1]PET bottle used: CSD, PCO 1881 neck finish, 591 ml.
[2]No. of specimens: 24

Examination of the data in Table 6, shows that Example 1 has a better pass rate than Examples 2 and 3. However, it was conditioned at room temperature (22° C.+/−1° C.) for 24 hours. Next, the PET bottle neck finish including the closure, was cut out using a Secure-Pak™ neck finish cutting tool. The combined neck finish/closure system was attached in a sealed fit with a pressure tubing and gas pressure was introduced. The PET neck finish/closure system was placed into a testing fixture and the entire assembly was placed into a water tank of a Secure Seal Tester, model SST, manufactured by Secure Pak (Maumee, Ohio). The test was carried out in water at room temperature (22° C.). The pressure was slowly applied to the interior of the closure to 100 Psi and held for a period of 1 minute. The PET bottle neck finish-closure sample was observed for signs of air bubbles. A failure is indicated when a steady stream of bubbles emitting from the closure can be observed. In a next step, the pressure was increased to 175 psi and held for one 1 minute to again look for evidence of air bubbles. In a final step, the pressure was increased to 200 psi and held for 1 minute, and evidence of air bubbles was looked for. The pressures at which observable air leakage events occurred were recorded as well as the percentage of air passage.

A total of twenty Secure Seal tests were carried out for each of Examples 1-3 and the results are provided in Table 7.

Examination of the data in Table 7, shows that Examples 1 and 2, where the closure is made from a unimodal polyethylene composition (e.g., 2712CC) have inferior sealing properties when compared to Example 3, where the closure is made from a bimodal polyethylene composition. For Example 3, no failures were observed at pressures of up to 200 psi. For Example 1, only 10% of the closures passed the secure seal test at a pressure of more than 175 psi for more than 1 minute, while several began to fail at a pressure of below 175 psi.

Removal Torque Test

This is an International Society of Beverage Technologists (ISBT) voluntary standard test. It is used to determine the torque required to remove a closure from a container.

After filling and capping a PET bottle with 4.2 GV of $CO_2$ as described above, the bottle was conditioned for 24 hours at room temperature (22° C.+/−1° C.) prior to conducting the removal torque test. The total application angle used for testing was 740°. The maximum removal torque was tested using a Steinfurth automated torque measuring machine with a proper chuck at the speed of 0.8 rpm/minute. A total of twelve tests were carried out for each of Examples 1 to 3 and the average results are provided in Table 8.

TABLE 7

Secure Seal Test (SST) of a PET bottle - PE closure System
(closure has additives for color, 1% red, and slip, 1000 ppm by way of 2% masterbatch)

| Example | Specimen No. | P1 Leakage @ 100 psi, No. of failures | Maximum Pressure attained in psi with elapsed time before failure (seconds) | Specimen No. | P1 Leakage @ 100 psi, No. of failures | Maximum Pressure attained in psi with elapsed time before failure (seconds) |
|---|---|---|---|---|---|---|
| 1, Comp. | 1 | 0 | 175 (10 sec) | 11 | 0 | 175 (12 sec) |
| | 2 | 0 | 155 | 12 | 0 | 200 |
| | 3 | 0 | 175 (55 sec) | 13 | 0 | 175 (37 sec) |
| | 4 | 0 | 135 | 14 | 0 | 175 (10 sec) |
| | 5 | 0 | 175 (45 sec) | 15 | 0 | 175 (8 sec) |
| | 6 | 0 | 175 (0 sec) | 16 | 0 | 175 (4 sec) |
| | 7 | 0 | 180 | 17 | 0 | 165 |
| | 8 | 0 | 160 | 18 | 0 | 150 |
| | 9 | 0 | 175 (8 sec) | 19 | 0 | 160 |
| | 10 | 0 | 175 (42 sec) | 20 | 0 | 175 (9 sec) |
| | No. of specimens not lasting 175 psi for 1 minute = 18; % Pass >175 psi for 1 minute = 10% | | | | | |
| 2 | 1 | 0 | 180 | 11 | 0 | 200 |
| | 2 | 0 | 175 (28 sec) | 12 | 0 | 175 |
| | 3 | 0 | 200 | 13 | 0 | 200 |
| | 4 | 0 | 200 | 14 | 0 | 200 |
| | 5 | 0 | 200 | 15 | 0 | 200 |
| | 6 | 0 | 200 | 16 | 0 | 195 |
| | 7 | 0 | 200 | 17 | 0 | 200 |
| | 8 | 0 | 200 | 18 | 0 | 200 |
| | 9 | 0 | 200 | 19 | 0 | 200 |
| | 10 | 0 | 200 | 20 | 0 | 175 (28 sec) |
| | No. of specimens not lasting 175 psi for 1 minute = 2; % Pass >175 psi for 1 minute = 90%, 2 specimens did not get to 175 psi for one minute and 4 specimens did not achieve 200 psi. | | | | | |
| 3 | 1 | 0 | 200 | 11 | 0 | 200 |
| | 2 | 0 | 200 | 12 | 0 | 200 |
| | 3 | 0 | 200 | 13 | 0 | 200 |
| | 4 | 0 | 200 | 14 | 0 | 200 |
| | 5 | 0 | 200 | 15 | 0 | 200 |
| | 6 | 0 | 200 | 16 | 0 | 200 |
| | 7 | 0 | 200 | 17 | 0 | 200 |
| | 8 | 0 | 200 | 18 | 0 | 200 |
| | 9 | 0 | 200 | 19 | 0 | 200 |
| | 10 | 0 | 200 | 20 | 0 | 200 |
| | No. of specimens not lasting 175 psi for 1 minute = 0; % Pass >175 psi for 1 minute = 100% | | | | | |

TABLE 8[1]

Removal Torque of a PET Bottle - PE Closure System
(closure has additives for color, 1% red, and slip, 1000
ppm by way of 2% masterbatch)

| Example | Average (in-lb) | Std. Dev. (in-lb) | Minimum (in-lb) | Maximum (in-lb) |
|---|---|---|---|---|
| 1, Comp. | 12.6 | 0.88 | 11.7 | 14.4 |
| 2 | 12.3 | 0.81 | 11.4 | 13.5 |
| 3 | 13.9 | 0.96 | 12.1 | 15.3 |

Note
[1]PET bottle used: CSD, PCO 1881 neck finish, 591 ml.

The data in Table 8, support the notion that the polyethylene composition in Example 3 leads to superior closure performance than the unimodal polyethylene compositions of Examples 1 and 2 (e.g., SCLAIR 2712 and SCLAIR 2807). For Example 3, the average removal torque is 13.9 inches pound, compared to 12.6 and 12.3 inches pound for Examples 1 and 2 respectively. Also, the minimum toque to remove the closure of Example 3 is higher than that required for the closures made with SCLAIR 2712 or SCLAIR 2807 which is indicative of improved sealing properties.

Ball Impact Test

This is an International Society of Beverage Technologists (ISBT) voluntary standard test. During transportation and use by the consumer, a beverage closure can experience impact forces. The ball impact test evaluates the tendency of the closure to remain on a container opening without release. The test was carried out as follows. After filling and capping a PET bottle-closure system with 4.2 GV of $CO_2$ as described above, the bottle-closure system was conditioned for 24 hours in a temperature controlled chamber at 4° C. Ball impact testing was conducted using Steinfurth Ball impact tester which holds the bottle-closure system against movement with the bottle-closure system held in a desired orientation. A steel ball (286.7 g, 41.27 mm in diameter) was used as the impacting object. The steel ball was dropped from a height of 762 mm (30 inches) at four different orientations; at 0° to the top center of the closure, at 90° to the top edge of the closure, at 45° to top edge of the closure, and at 90° to the sidewall edge of the closure. After the impact test, the bottle-closure system was removed from the impact tester and the closure was checked for damage and/or leakage. A total of ten ball impact tests were carried out at each angle for each of Examples 1 to 3 and the results are provided in Table 9.

The data in Table 9 show that the closure of Example 3 has the best ball impact performance with a nearly 100 percent pass rate. Next best is the closure of Example 2, which passed 72.5 percent of the ball impact tests. Finally, the worst performer is the closure of Example 1 with the lowest overall pass rate of 70% and a particularly poor performance when the ball impact test is carried out at 90° to the top edge of the closure (pass rate of only 30%).

Non-limited embodiments of the present disclosure include the following:

Embodiment A

A process to fill a container, the process comprising: adding a hot liquid to the container through a container opening, sealing the container opening with a closure comprising a high density polyethylene composition, and bringing the hot liquid into contact with an interior surface of the closure; wherein the high density polyethylene composition comprises:

(1) about 10 to about 70 wt % of a first ethylene copolymer having a melt index $I_2$, of from 0.1 to 10 g/10 min; a molecular weight distribution $M_w/M_n$, of less than 2.7; and a density of from 0.930 to 0.960 g/cm$^3$; and (2) about 90 to about 30 wt % of a second ethylene copolymer having a melt index $I_2$, of from 50 to 10,000 g/10 min; a molecular weight distribution $M_w/M_n$, of less than 2.7; and a density higher than the density of the first ethylene copolymer, but less than 0.966 g/cm$^3$;

wherein the density of the second ethylene copolymer is less than 0.037 g/cm$^3$ higher than the density of the first ethylene copolymer; the ratio (SCB1/SCB2) of the number of short chain branches per thousand carbon atoms in the first ethylene copolymer (SCB1) to the number of short chain branches per thousand carbon atoms in the second ethylene copolymer (SCB2) is greater than 1.0; and wherein the polyethylene composition has a molecular weight distribution $M_w/M_n$, of from 2.0 to 7.0; a density of at least 0.950 g/cm$^3$; and a melt index $I_2$, of greater than 3.0 to less than 20.0 g/10 min.

Embodiment B

The process of Embodiment A wherein the high density polyethylene composition has a high load melt index $I_{21}$, of from 150 to 400 g/10 min

TABLE 9[1]

Ball Impact Test of PET Bottle - PE Closure System
(closure has additives for color, 1% red, and slip, 1000 ppm by way of 2% masterbatch)

| Example | 0° to top center of closure No. of failure (% of pass) | 90° to top edge of closure No. of failure (% of pass) | 45° angle to top edge of closure No. of failure (% of pass) | 90° to sidewall edge of closure No. of failure (% of pass) | Total No. of failures % of pass |
|---|---|---|---|---|---|
| 1, Comp. | 0 (100%) | 7 (30%) | 1 (90%) | 4 (60%) | 12 (70%) |
| 2 | 0 (100%) | 6 (40%) | 4 (60%) | 1 (90%) | 11 (72.5%) |
| 3 | 0 (100%) | 1 (90%) | 0 (100%) | 0 (100%) | 1 (97.5%) |

Note
[1]PET bottle used: CSD, PCO 1881 neck finish, 591 ml.

Embodiment C

The process of Embodiment A or B wherein the high density polyethylene composition has a Z-average molecular weight, $M_z$ of less than about 300,000.

Embodiment D

The process of Embodiment A, B or C wherein the high density polyethylene composition has a melt flow ratio, $I_{21}/I_2$ of from 22 to 50

Embodiment E

The process of Embodiment A, B, C or D wherein the high density polyethylene composition has and an ESCR Condition B (100% IGEPAL) of at least about 3.5 hrs.

Embodiment F

The process of Embodiment A, B, C, D or E wherein the high density polyethylene composition has a TD/MD shrinkage ratio of from about 0.90 to about 1.15 when measured according to the Dimensional Stability Test (DST).

Embodiment G

The process of Embodiment A, B, C, D, E or F wherein the first and second ethylene copolymers are made by polymerizing ethylene and an alpha olefin in the presence of a single site catalyst.

Embodiment H

The process of Embodiment A, B, C, D, E, F or G wherein the first ethylene copolymer has a density of from 0.936 to 0.952 g/cm³.

Embodiment I

The process of Embodiment A, B, C, D, E, F, G or H wherein the second ethylene copolymer has a density of less than 0.965 g/cm³.

Embodiment J

The process of Embodiment A, B, C, D, E, F, G, H or I wherein the high density polyethylene composition has a density of from 0.952 to 0.960 g/cm³.

Embodiment K

The process of Embodiment A, B, C, D, E, F, G, H, I or J wherein the density of the second ethylene copolymer is less than 0.030 g/cm³ higher than the density of the first ethylene copolymer.

Embodiment L

The process of Embodiment A, B, C, D, E, F, G, H, I, J or K wherein the first and second ethylene copolymers have a $M_w/M_n$ of less than 2.3.

Embodiment M

The process of Embodiment A, B, C, D, E, F, G, H, I, J, K or L wherein the high density polyethylene composition comprises: from about 25 to about 60 wt % of the first ethylene copolymer; and from about 75 to about 40 wt % of the second ethylene copolymer.

Embodiment N

The process of Embodiment A, B, C, D, E, F, G, H, I, J, K, L or M wherein the high density polyethylene composition further comprises a nucleating agent or a combination of nucleating agents.

Embodiment O

The process of Embodiment A, B, C, D, E, F, G, H, I, J, K, L, M or N wherein the first and second ethylene copolymers are copolymers of ethylene and 1-octene.

Embodiment P

The process of Embodiment A, B, C, D, E, F, G, H, I, J, K, L, M, N or O wherein the closure is made by continuous compression molding or injection molding.

Embodiment Q

The process of Embodiment A, B, C, D, E, F, G, H, I, J, K, L, M, N, O or P wherein the high density polyethylene composition is prepared by contacting ethylene and an alpha-olefin with a polymerization catalyst under solution polymerization conditions in a least two polymerization reactors.

Embodiment R

The process of Embodiment A, B, C, D, E, F, G, H, I, J, K, L, M, N, O, P or Q claim 1 wherein high density polyethylene composition has a stress exponent of less than 1.40.

Embodiment S

Use of a closure in a hot fill process, wherein the closure comprises a high density polyethylene composition comprising:

(1) about 10 to about 70 wt % of a first ethylene copolymer having a melt index $I_2$, of from 0.1 to 10 g/10 min; a molecular weight distribution $M_w/M_n$, of less than 2.7; and a density of from 0.930 to 0.960 g/cm³; and (2) about 90 to about 30 wt % of a second ethylene copolymer having a melt index $I_2$, of from 50 to 10,000 g/10 min; a molecular weight distribution $M_w/M_n$, of less than 2.7; and a density higher than the density of the first ethylene copolymer, but less than 0.966 g/cm³;

wherein the density of the second ethylene copolymer is less than 0.037 g/cm³ higher than the density of the first ethylene copolymer; the ratio (SCB1/SCB2) of the number of short chain branches per thousand carbon atoms in the first ethylene copolymer (SCB1) to the number of short chain branches per thousand carbon atoms in the second ethylene copolymer (SCB2) is greater than 1.0; and wherein the polyethylene composition has a molecular weight distribution $M_w/M_n$, of from 2.0 to 7.0; a density of at least 0.950 g/cm³; and a melt index $I_2$, of greater than 3.0 to less than 20.0 g/10 min.

Embodiment T

The use of a closure according to Embodiment S wherein the high density polyethylene composition has a high load melt index $I_{21}$, of from 150 to 400 g/10 min.

Embodiment U

The use of a closure according to Embodiment S or T wherein the high density polyethylene composition has a Z-average molecular weight, $M_Z$ of less than about 300,000.

Embodiment V

The use of a closure according to Embodiment S, T or U wherein the high density polyethylene composition has a melt flow ratio, $I_{21}/I_2$ of from 22 to 50.

Embodiment W

The use of a closure according to Embodiment S, T, U or V wherein the high density polyethylene composition has and an ESCR Condition B (100% IGEPAL) of at least about 3.5 hours.

Embodiment X

The use of a closure according to Embodiment S, T, U, V or W wherein the high density polyethylene composition has a TD/MD shrinkage ratio of from about 0.90 to about 1.15 when measured according to the Dimensional Stability Test (DST).

Embodiment Y

The use of a closure according to Embodiment S, T, U, V, W, or X wherein the first and second ethylene copolymers are made by polymerizing ethylene and an alpha olefin in the presence of a single site catalyst.

Embodiment Z

The use of a closure according to Embodiment S, T, U, V, W, X or Y wherein the first ethylene copolymer has a density of from 0.936 to 0.952 g/cm³.

Embodiment AA

The use of a closure according to Embodiment S, T, U, V, W, X, Y or Z wherein the second ethylene copolymer has a density of less than 0.965 g/cm³.

Embodiment BB

The use of a closure according to Embodiment S, T, U, V, W, X, Y, Z or AA wherein the high density polyethylene composition has a density of from 0.952 to 0.960 g/cm³.

Embodiment CC

The use of a closure according to Embodiment S, T, U, V, W, X, Y, Z, AA or BB wherein the density of the second ethylene copolymer is less than 0.030 g/cm³ higher than the density of the first ethylene copolymer.

Embodiment DD

The use of a closure according to Embodiment S, T, U, V, W, X, Y, Z, AA, BB or CC wherein the first and second ethylene copolymers have a $M_w/M_n$ of less than 2.3.

Embodiment EE

The use of a closure according to Embodiment S, T, U, V, W, X, Y, Z, AA, BB, CC, or DD wherein the high density polyethylene composition comprises: from about 25 to about 60 wt % of the first ethylene copolymer; and from about 75 to about 40 wt % of the second ethylene copolymer.

Embodiment FF

The use of a closure according to Embodiment S, T, U, V, W, X, Y, Z, AA, BB, CC, DD or EE wherein the high density polyethylene composition further comprises a nucleating agent or a combination of nucleating agents.

Embodiment GG

The use of a closure according to Embodiment S, T, U, V, W, X, Y, Z, AA, BB, CC, DD, EE, or FF wherein the first and second ethylene copolymers are copolymers of ethylene and 1-octene.

Embodiment HH

The use of a closure according to Embodiment S, T, U, V, W, X, Y, Z, AA, BB, CC, DD, EE, FF or GG wherein the closure is made by continuous compression molding or injection molding.

Embodiment II

The use of a closure according to Embodiment S, T, U, V, W, X, Y, Z, AA, BB, CC, DD, EE, FF, GG or HH wherein the high density polyethylene composition is prepared by contacting ethylene and an alpha-olefin with a polymerization catalyst under solution polymerization conditions in a least two polymerization reactors.

Embodiment JJ

The use of a closure according to Embodiment S, T, U, V, W, X, Y, Z, AA, BB, CC, DD, EE, FF, GG, HH or II wherein high density polyethylene composition has a stress exponent of less than 1.40.

Embodiment KK

A process to fill a container, the process comprising: adding a hot liquid to the container through a container opening; sealing the container opening with a closure comprising a high density polyethylene composition which is bimodal and has a density of at least 0.950 g/cm³, a molecular weight distribution $M_w/M_n$, of from 2.0 to 7.0, and a melt index $I_2$, of from higher than 3.0 g/10 min to less than 20.0 g/10 min; and bringing the hot liquid into contact with an interior surface of the closure; wherein the closure has a time exponent, m of 0.105 or less where m is determined using a compressive strain model represented by the equation:

$$\varepsilon = A \times \sigma^n \times t^m$$

where ε is the compressive strain; σ is the stress in N/cm², t is the loading time in seconds, A is the model coefficient, n is the deformation stress exponent and m is the time exponent.

Embodiment LL

Use of a closure in a hot fill process, wherein the closure comprises a high density polyethylene composition which is bimodal and has a density of at least 0.950 g/cm³, a molecular weight distribution $M_w/M_n$, of from 2.0 to 7.0, and a melt index $I_2$, of from higher than 3.0 g/10 min to less than 20.0 g/10 min; wherein the closure has a time exponent, m of 0.105 or less, where m is determined using a compressive strain model represented by the equation:

$$\varepsilon = A \times \sigma^n \times t^m$$

where ε is the compressive strain; σ is the stress in N/cm², t is the loading time in seconds, A is the model coefficient, n is the deformation stress exponent and m is the time exponent.

Embodiment MM

A process to fill a container, the process comprising: adding a hot liquid to the container through a container opening, sealing the container opening with a closure comprising a high density polyethylene composition which is bimodal and has a density of at least 0.950 g/cm³, a molecular weight distribution $M_w/M_n$, of from 2.0 to 7.0, and a melt index $I_2$, of from higher than 3.0 g/10 min to less than 20.0 g/10 min; and bringing the hot liquid into contact with an interior surface of the closure.

Embodiment NN

Use of a closure in a hot fill process is provided, wherein the closure comprises a high density polyethylene composition which is bimodal and has a density of at least 0.950 g/cm³, a molecular weight distribution $M_w/M_n$, of from 2.0 to 7.0, and a melt index $I_2$, of from higher than 3.0 g/10 min to less than 20.0 g/10 min.

The embodiments of the invention in which an exclusive property or privilege is claimed are defined as follows:

What is claimed is:

1. A process to fill a container, the process comprising: adding a hot liquid to the container through a container opening, sealing the container opening with a closure comprising a high density polyethylene composition, and bringing the hot liquid into contact with an interior surface of the closure; wherein the high density polyethylene composition comprises:
   (1) about 10 to about 70 wt % of a first ethylene copolymer having a melt index $I_2$, of from 0.1 to 10 g/10 min; a molecular weight distribution $M_w/M_n$, of less than 2.7; and a density of from 0.930 to 0.960 g/cm³; and
   (2) about 90 to about 30 wt % of a second ethylene copolymer having a melt index $I_2$, of from 50 to 10,000 g/10 min; a molecular weight distribution $M_w/M_n$, of less than 2.7; and a density higher than the density of the first ethylene copolymer, but less than 0.966 g/cm³;

wherein the density of the second ethylene copolymer is less than 0.037 g/cm³ higher than the density of the first ethylene copolymer; the ratio (SCB1/SCB2) of the number of short chain branches per thousand carbon atoms in the first ethylene copolymer (SCB1) to the number of short chain branches per thousand carbon atoms in the second ethylene copolymer (SCB2) is greater than 1.0; and wherein the polyethylene composition has a molecular weight distribution $M_w/M_n$, of from 2.0 to 7.0; a density of at least 0.950 g/cm³; and a melt index $I_2$, of greater than 3.0 to less than 20.0 g/10 min.

2. The process of claim 1 wherein the high density polyethylene composition has a high load melt index $I_{21}$, of from 150 to 400 g/10 min.

3. The process of claim 1 wherein the high density polyethylene composition has a Z-average molecular weight, $M_z$ of less than about 300,000.

4. The process of claim 1 wherein the high density polyethylene composition has a melt flow ratio, $I_{21}/I_2$ of from 22 to 50.

5. The process of claim 1 wherein the high density polyethylene composition has and an ESCR Condition B (100% IGEPAL) of at least about 3.5 hours.

6. The process of claim 1 wherein the high density polyethylene composition has a TD/MD shrinkage ratio of from about 0.90 to about 1.15 when measured according to the Dimensional Stability Test (DST).

7. The process of claim 1 wherein the first and second ethylene copolymers are made by polymerizing ethylene and an alpha olefin in the presence of a single site catalyst.

8. The process of claim 1 wherein the first ethylene copolymer has a density of from 0.936 to 0.952 g/cm³.

9. The process of claim 1 wherein the second ethylene copolymer has a density of less than 0.965 g/cm³.

10. The process of claim 1 wherein the high density polyethylene composition has a density of from 0.952 to 0.960 g/cm³.

11. The process of claim 1 wherein the density of the second ethylene copolymer is less than 0.030 g/cm³ higher than the density of the first ethylene copolymer.

12. The process of claim 1 wherein the first and second ethylene copolymers have a $M_w/M_n$ of less than 2.3.

13. The process of claim 1 wherein the high density polyethylene composition comprises:
   from about 25 to about 60 wt % of the first ethylene copolymer; and
   from about 75 to about 40 wt % of the second ethylene copolymer.

14. The process of claim 1 wherein the high density polyethylene composition further comprises a nucleating agent or a combination of nucleating agents.

15. The process of claim 1 wherein the first and second ethylene copolymers are copolymers of ethylene and 1-octene.

16. The process of claim 1 wherein the closure is made by continuous compression molding or injection molding.

17. The process of claim 1 wherein the high density polyethylene composition is prepared by contacting ethylene and an alpha-olefin with a polymerization catalyst under solution polymerization conditions in a least two polymerization reactors.

18. The process of claim 1 wherein high density polyethylene composition has a stress exponent of less than 1.40.

19. Use of a closure in a hot fill process, wherein the closure comprises a high density polyethylene composition comprising:

(1) about 10 to about 70 wt % of a first ethylene copolymer having a melt index $I_2$, of from 0.1 to 10 g/10 min; a molecular weight distribution $M_w/M_n$, of less than 2.7; and a density of from 0.930 to 0.960 g/cm³; and (2) about 90 to about 30 wt % of a second ethylene copolymer having a melt index $I_2$, of from 50 to 10,000 g/10 min; a molecular weight distribution $M_w/M_n$, of less than 2.7; and a density higher than the density of the first ethylene copolymer, but less than 0.966 g/cm³; wherein the density of the second ethylene copolymer is less than 0.037 g/cm³ higher than the density of the first ethylene copolymer; the ratio (SCB1/SCB2) of the number of short chain branches per thousand carbon atoms in the first ethylene copolymer (SCB1) to the number of short chain branches per thousand carbon atoms in the second ethylene copolymer (SCB2) is greater than 1.0; and wherein the polyethylene composition has a molecular weight distribution $M_w/M_n$, of from 2.0 to 7.0; a density of at least 0.950 g/cm³; and a melt index $I_2$, of greater than 3.0 to less than 20.0 g/10 min.

20. The use of a closure according to claim 19 wherein the high density polyethylene composition has a high load melt index $I_{21}$, of from 150 to 400 g/10 min.

21. The use of a closure according to claim 19 wherein the high density polyethylene composition has a Z-average molecular weight, $M_Z$ of less than about 300,000.

22. The use of a closure according to claim 19 wherein the high density polyethylene composition has a melt flow ratio, $I_{21}/I_2$ of from 22 to 50.

23. The use of a closure according to claim 19 wherein the high density polyethylene composition has and an ESCR Condition B (100% IGEPAL) of at least about 3.5 hours.

24. The use of a closure according to claim 19 wherein the high density polyethylene composition has a TD/MD shrinkage ratio of from about 0.90 to about 1.15 when measured according to the Dimensional Stability Test (DST).

25. The use of a closure according to claim 19 wherein the first and second ethylene copolymers are made by polymerizing ethylene and an alpha olefin in the presence of a single site catalyst.

26. The use of a closure according to claim 19 wherein the first ethylene copolymer has a density of from 0.936 to 0.952 g/cm³.

27. The use of a closure according to claim 19 wherein the second ethylene copolymer has a density of less than 0.965 g/cm³.

28. The use of a closure according to claim 19 wherein the high density polyethylene composition has a density of from 0.952 to 0.960 g/cm³.

29. The use of a closure according to claim 19 wherein the density of the second ethylene copolymer is less than 0.030 g/cm³ higher than the density of the first ethylene copolymer.

30. The use of a closure according to claim 19 wherein the first and second ethylene copolymers have a $M_w/M_n$ of less than 2.3.

31. The use of a closure according to claim 19 wherein the high density polyethylene composition comprises:
from about 25 to about 60 wt % of the first ethylene copolymer; and
from about 75 to about 40 wt % of the second ethylene copolymer.

32. The use of a closure according to claim 19 wherein the high density polyethylene composition further comprises a nucleating agent or a combination of nucleating agents.

33. The use of a closure according to claim 19 wherein the first and second ethylene copolymers are copolymers of ethylene and 1-octene.

34. The use of a closure according to claim 19 wherein the closure is made by continuous compression molding or injection molding.

35. The use of a closure according to claim 19 wherein the high density polyethylene composition is prepared by contacting ethylene and an alpha-olefin with a polymerization catalyst under solution polymerization conditions in a least two polymerization reactors.

36. The use of a closure according to claim 19 wherein high density polyethylene composition has a stress exponent of less than 1.40.

37. A process to fill a container, the process comprising: adding a hot liquid to the container through a container opening; sealing the container opening with a closure comprising a high density polyethylene composition which is bimodal and has a density of at least 0.950 g/cm³, a molecular weight distribution $M_w/M_n$, of from 2.0 to 7.0, and a melt index $I_2$, of from higher than 3.0 g/10 min to less than 20.0 g/10 min; and bringing the hot liquid into contact with an interior surface of the closure; wherein the closure has a time exponent, m of 0.105 or less where m is determined using a compressive strain model represented by the equation:

$$\varepsilon = A \times \sigma^n \times t^m$$

where ε is the compressive strain; σ is the stress in N/cm², t is the loading time in seconds, A is the model coefficient, n is the deformation stress exponent and m is the time exponent.

38. Use of a closure in a hot fill process, wherein the closure comprises a high density polyethylene composition which is bimodal and has a density of at least 0.950 g/cm³, a molecular weight distribution $M_w/M_n$, of from 2.0 to 7.0, and a melt index $I_2$, of from higher than 3.0 g/10 min to less than 20.0 g/10 min; wherein the closure has a time exponent, m of 0.105 or less, where m is determined using a compressive strain model represented by the equation:

$$\varepsilon = A \times \sigma^n \times t^m$$

where ε is the compressive strain; σ is the stress in N/cm², t is the loading time in seconds, A is the model coefficient, n is the deformation stress exponent and m is the time exponent.

* * * * *